United States Patent
Bechtel et al.

(10) Patent No.: US 8,543,180 B2
(45) Date of Patent: *Sep. 24, 2013

(54) METHOD AND APPARATUS FOR TOTAL HEMOGLOBIN MEASUREMENT

(75) Inventors: Kate Leeann Bechtel, Pleasant Hill, CA (US); Tobias Funk, Martinez, CA (US); Brian Patrick Wilfley, Los Altos, CA (US); Joseph Anthony Heanue, Oakland, CA (US)

(73) Assignee: Covidien LP, Mansfield, MA (US)

( * ) Notice: Subject to any disclaimer, the term of this patent is extended or adjusted under 35 U.S.C. 154(b) by 383 days.

This patent is subject to a terminal disclaimer.

(21) Appl. No.: 12/875,983

(22) Filed: Sep. 3, 2010

(65) Prior Publication Data
US 2011/0118572 A1    May 19, 2011

Related U.S. Application Data

(63) Continuation-in-part of application No. 11/381,443, filed on May 3, 2006.

(51) Int. Cl.
*A61B 5/1455* (2006.01)

(52) U.S. Cl.
USPC ............ 600/328; 600/310; 600/322; 600/323

(58) Field of Classification Search
USPC ................. 600/310, 322, 323, 326, 328, 330, 600/331, 340, 473, 476; 356/41
See application file for complete search history.

(56) References Cited

U.S. PATENT DOCUMENTS

| | | | | |
|---|---|---|---|---|
| 5,101,825 A | * | 4/1992 | Gravenstein et al. | 600/326 |
| 5,155,741 A | * | 10/1992 | Waters et al. | 375/142 |
| 5,497,769 A | * | 3/1996 | Gratton et al. | 600/323 |
| 6,236,483 B1 | * | 5/2001 | Dutt et al. | 398/141 |
| 6,616,353 B1 | * | 9/2003 | Helkey | 356/450 |
| 2005/0187451 A1 | * | 8/2005 | Norris | 600/326 |
| 2011/0066014 A1 | * | 3/2011 | Bechtel et al. | 600/323 |

* cited by examiner

*Primary Examiner* — Eric Winakur
*Assistant Examiner* — Chu Chuan (JJ) Liu

(57) ABSTRACT

The present invention pertains to a method and apparatus for total hemoglobin measurement. A modulated optical signal based on a digital code sequence is transmitted to human tissue. A temporal transfer characteristic is derived from the modulated optical signal. Total hemoglobin is determined based on the temporal transfer characteristic.

16 Claims, 11 Drawing Sheets

METHOD AND APPARATUS FOR TOTAL HEMOGLOBIN MEASUREMENT

CROSS REFERENCE TO RELATED APPLICATIONS

The present application is a continuation-in-part of U.S. patent application Ser. No. 11/381,443, filed on May 3, 2006, entitled "Method and Apparatus for Lymph Node Mapping," which is incorporated herein by reference.

FIELD OF THE INVENTION

The field of the present invention pertains generally to optical imaging using near-infrared light, including more specifically, to the optical detection of sentinel lymph node location in order to guide surgical procedures.

BACKGROUND

Sentinel lymph node biopsy is a surgical procedure that involves removing a small sample of lymph tissue and examining it for signs of cancer. As an alternative to conventional full lymph node dissection, it is increasingly used as the standard of care in the staging of breast cancer and melanoma. The sentinel lymph node (SLN) is the first node, or group of nodes, in the lymphatic network to come into contact with metastatic cancer cells that have spread from the primary tumor site. SLN biopsy allows a physician to obtain information about the other lymph nodes in the network without exposing the patient to the risks of conventional surgery. Further surgery to remove other lymph nodes may be avoided if no cancer cells are found in the sentinel lymph nodes.

SLN biopsy usually begins with the injection of a radioactive tracer (technetium-99 sulfur colloid), a blue dye, or both into the area around the original cancer site. Lymphatic vessels carry the tracer to the sentinel node (or nodes); this is the lymph node most likely to contain cancer cells. Prior to surgery, a wide field-of-view gamma camera is typically used to image the location of the radiotracer. Images are generally taken from multiple positions and perspectives, resulting in a map of the drainage pattern of lymphatic fluid from the skin to the lymph nodes. By showing where the cancer is likely to have spread, the map enables the surgeon to plan the full procedure prior to the first incision. During surgery, the surgeon achieves further guidance either through direct visualization of the injected blue dye or by detecting the radioactive tracer with a hand-held gamma probe. After surgery, the lymph node is sent for pathological examination that can include microscopic inspection, tissue culture, or immunological tests.

The current approach of using radioisotopes for SLN mapping has several drawbacks. First, while the radiation risk to patients and medical practitioners is relatively low compared to other medical procedures, the handling of radioisotopes still requires special precautions. Second, the procedure requires the coordination of both surgical and nuclear medicine personnel, resulting in both scheduling issues and increased cost. Lastly, the time required for the radiotracer to travel through the lymphatic system can be as long as several hours. It is highly desirable to have an alternative system that could be used without radiotracers and that a surgeon could utilize without the involvement of other specialists. It is also desirable to have a system that uses a contrast agent with more rapid kinetics.

Diffuse optical imaging techniques are known in medical and biological applications. Overviews of diffuse optical imaging techniques can be found in "Recent Advances in Diffusion Optical Imaging" by Gibson, et al, Phys. Med. Biology, vol. 50 (2005), R1-R43 and in "Near-infrared Diffuse Optical Tomography," by Hielscher, et al, Disease Markers, Vol. 18 (2002), 313-337. Briefly, diffuse optical imaging involves the use of near-infrared light incident upon a sample of interest. An example in the medical and biological field is optical mammography where near infrared light is used to illuminate breast tissue. A detector is placed on the opposite side of the breast from the incident light some distance away and collects scattered light from the breast tissue. The scattered light of interest that is detected may be directly scattered incident light or scattered fluorescence light caused by the excitation of an injected fluorescing material that fluoresces when exposed to the incident light. By measuring the amplitude of the light of interest at the detector and the distribution of photon arrival times at the detector for various source and detector positions, a reconstruction of the underlying tissue optical properties can be made. An overview of image reconstruction techniques can be found in the citations given in the aforementioned review articles.

Measurements of the photon flight-time distributions are typically carried out using either a time-domain or a frequency-domain technique. In the time-domain technique, the sample is excited with pulse of light from a pulsed laser and the scattered light is measured using a detector with single-photon sensitivity. The detector measures the time delay between the excitation pulse and the first detected photon. The flight-time distribution is determined by using many repeated pulses and building up a histogram of the measured time delays. Unfortunately, the pulsed laser sources and single-photon detectors are relatively expensive. Because detection is typically done at the single-photon level, it can require a significant amount of time to build-up enough data to approximate the flight-time distribution. One disadvantage of the frequency-domain approach is that it is not a direct measurement of the photon flight time. Rather, it provides an estimate of the mean flight time based on the phase shift between a detected signal and the excitation signal. In some cases, more accurate image reconstructions can be obtained using more complete measurements of the flight-time distributions. This data is not readily obtained with frequency-domain instrumentation. A further disadvantage of the frequency-domain approach is the need for accurate high-frequency analog electronics. An overview of both the time-domain and frequency-domain techniques can be found in the above-referenced article by Hielscher, et al.

U.S. Pat. No. 5,565,982 discloses a time-resolved spectroscopy system using digital processing techniques and two low power, continuous wave light sources. The disclosed system requires two light transmitters of different wavelengths modulated with separate codes for interrogating a sample of interest. Properties of the sample are inferred by differential comparison of the return signals from each of the two light sources. It is undesirable to have two distinct light sources due to the cost and complexity involved. Furthermore, the noise level associated with a measurement made with two separate light sources will be higher than with a single source even if the codes used to drive the two sources are orthogonal. It is desirable to have a means of interrogating a particular tissue volume with a single light source at one wavelength in order to obtain temporal information.

What is needed is an imaging system capable of sentinel lymph node mapping that does not require the use of radiotracers. Furthermore, the system should be implemented with low-power continuous-wave light sources and digital electronics.

SUMMARY

The present invention pertains to a method and apparatus for total hemoglobin measurement. The total hemoglobin measurement system has a signal generator for generating a digital modulation signal representing a code sequence and an optical illumination source for receiving the digital modulation signal and for transmitting a modulated optical signal along an optical transmission path to human tissue in response to the digital modulation signal. The total hemoglobin measurement system also has a detector for receiving the modulated optical signal after transmission through human tissue and a processor for deriving a temporal transfer characteristic for the optical signal and for determining the oxygen level based on the temporal transfer characteristic. In another embodiment, a method for measuring total hemoglobin involves generating a digital modulation signal associated with a code sequence and generating a modulated optical signal based on the digital modulation signal. It also involves transmitting the modulated optical signal to human tissue and receiving a modified version of the modulated optical signal after transmission through human tissue. It also involves deriving a temporal transfer characteristic for the modified version of the modulated optical signal and calculating total hemoglobin based on the temporal transfer characteristic.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
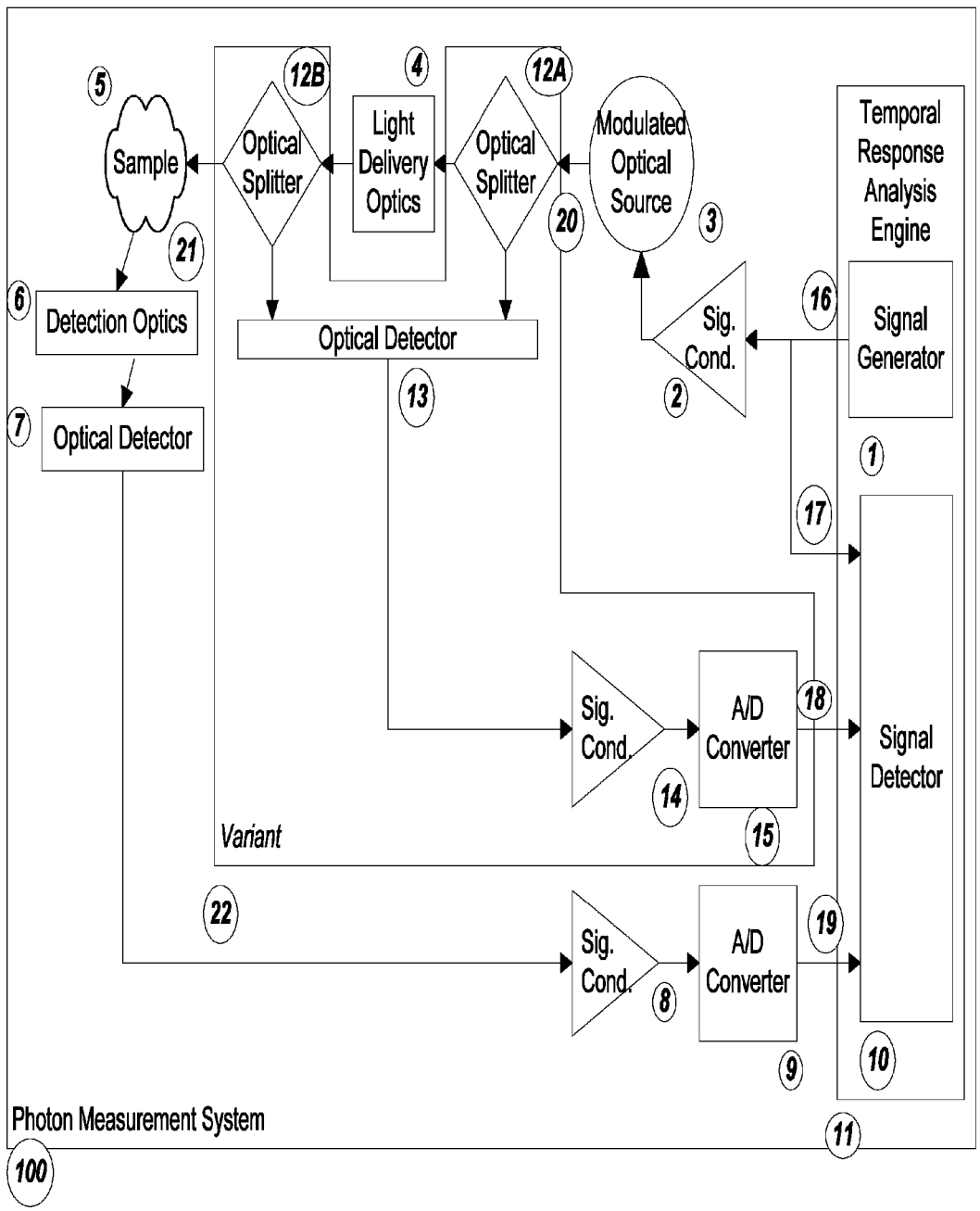
FIG. 1 is a functional block diagram of the major components of a preferred photon measurement system of the present invention.

A functional block diagram of a preferred photon measurement system 100 is depicted in FIG. 1. The photon measurement system can be used to measure the interaction of photons with a sample 5. In certain applications, the sample 5 may be human breast tissue or fat tissue but it could just as well be any semitransparent material. The photon measurement system 100 preferably includes Temporal Response Analysis Engine 11. The Temporal Response Analysis Engine 11 generates a digital modulation signal for driving an illumination light source that is used to interrogate the sample. The Temporal Response Engine 11 also provides a means for processing a detected optical signal from the sample 5 to extract information about the sample 5. Preferably a digital modulation signal 16 is generated in the signal generator 1 and transmitted to the transmit signal conditioner 2. The digital modulation signal 16 is the digital representation of a chosen code sequence. The code sequence is preferably chosen from the known pseudorandom binary sequences (PRBS), Gold codes, Golay codes, Kasami codes, Walsh codes, or other codes that possess the preferred desirable property of large auto-correlation values and low cross-correlation values. The digital modulation signal 16 may represent a single code pattern or multiple repeats of the same pattern. A single complete set of code patterns is designated a modulation frame or code pattern frame. The digital modulation signal 16 is preferably transmitted to the signal detector 10 as an electronic reference signal 17. The transmit signal conditioner 2 formats the digital modulation signal 16 as necessary to drive an optical illumination source 3. In the preferred photon measurement system 100, the modulated optical source is a 785 nm diode laser made by Hitachi Corp. Formatting of the digital modulation signal 16 in the preferred embodiment involves converting the digital modulation signal 16 to an analog voltage waveform that is coupled through a 50-ohm bias-T to the DC drive current of the optical illumination source 3. In other embodiments, the optical illumination source 3 may be a different laser diode, a light-emitting diode, or a light source used together with an external optical modulator. The optical illumination source 3 generates the modulated optical wave 20 which is preferably transmitted to the sample 5 by light delivery optics 4. The preferred light delivery optics 4 is a 3 mm diameter fiber bundle located between the optical illumination source 3 and the sample 5 to deliver the modulated optical wave 20 from the optical illumination source 3 to the sample 5. In other embodiments the light delivery optics 4 comprises other arrangements of optical fibers, lenses, mirrors or other optical delivery components. When the modulated optical wave 20 illuminates the sample 5 scattered optical waves 21 are generated. In the preferred photon measurement system, the sample 5 is treated with a fluorescent material that will fluoresce when it is illuminated by the modulated optical waves 20. In the preferred system the scattered optical waves 21 are fluorescence generated from a fluorescent material within the sample 5. The fluorescent material is preferably an exogenous contrast agent injected into the sample 5 or alternatively it is preferably some constituent component of a material that exhibits endogenous fluorescence. The detection optics 6 are situated so that a portion of the modulated optical waves 21 are detected by the detection optics 6. In the preferred photon measurement system 100, the detection optics 6 include an optical filter for separating the fluorescing scattered optical waves 21 from the modulated optical waves 20. The optical filter preferably transmits the higher wavelength fluorescence and blocks the lower wavelength illumination light. In applications where the scattered optical waves 21 of interest are not fluorescing, an optical filter is not required.

In the preferred photon measurement system 100, the detection optics 6 preferably include a second 3 mm diameter fiber bundle located between the optical filter and the optical detector 7. The optical detector 7 converts the scattered optical waves 21 to an electronic signal. In the preferred photon measurement system 100, the optical detector 7 is preferably a photomultiplier tube, model R7400U-20 from Hamamatsu Corp. In other embodiments, the optical detector 7 may be a PIN photodiode, an avalanche photodiode, a charge-couple device, or other suitable photosensitive element. As previously stated, the optical detector 7 preferably converts detected scattered optical waves 21 into an electronic signal which is communicated to the detected signal conditioner 8. The detected signal conditioner 8 preferably formats the signal so it may be converted to discrete samples by an Analog to Digital (A/D) converter 9. The A/D converter 9 outputs a detected response signal 19. The detected response signal 19 is communicated to a signal detector 10, where it is preferably correlated with the electronic reference signal 17 to extract a sample transfer characteristic.

Information about the temporal properties of the photons is preferably calculated from the sample transfer characteristic. This information preferably includes such properties as direct measurements of photon time-of-flight and the fluorescence lifetime. The estimate of photon times-of-flight is then preferably used to estimate characteristics of the tissue such as the absorption coefficient, scattering coefficient, or location of fluorescing material.

Another embodiment of the photon measurement system 100 includes an optical reference generator 22. The optical reference generator 22 preferably includes an optical splitter 12A or 12B that routes a portion of the modulated optical wave 20 to a secondary optical detector 13. The position of the optical splitter 12A or 12B can be either before or after the light delivery optics. The output of the secondary optical detector 13 is preferably routed to a secondary signal conditioner 14 whose output is communicated to a secondary A/D converter 15. The secondary A/D converter 15 preferably outputs a source reference signal 18 which can be correlated with the detected response 19 to extract the sample transfer characteristic. Using the source reference signal 18 as opposed to the electronic reference signal 17 allows the filtering of the temporal properties of the signal conditioner 2 and the modulated optical source 3 from the measured transfer characteristic.

Figure 2:
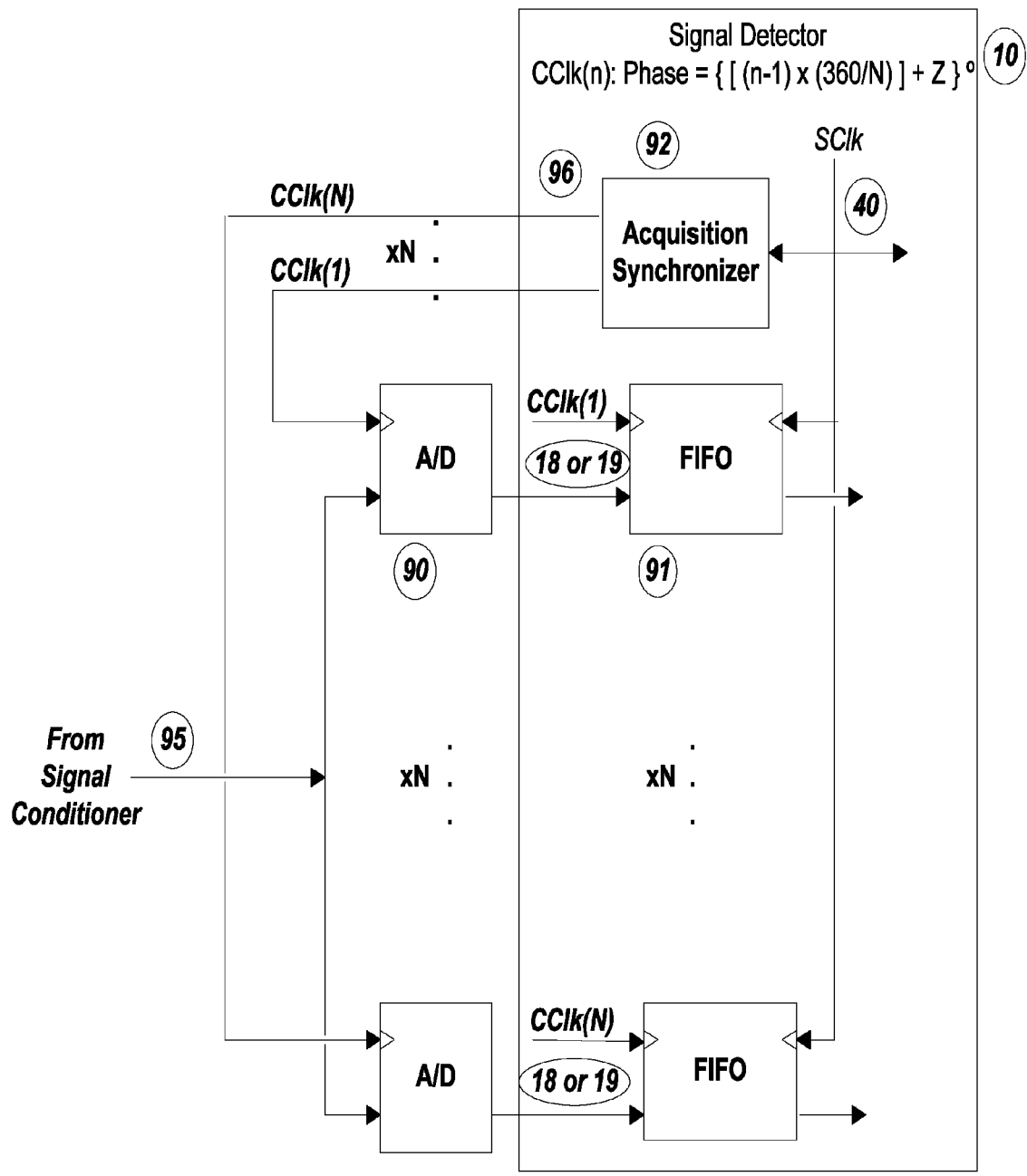
FIG. 2 is a diagram of preferred Analog-to-Digital converters and their interface to the signal detector.

The preferred hardware implementation of the A/D converter module and its interfaces to the signal detector 10 are shown in FIG. 2. An array of N A/D converters 90 preferably receives the analog signal 95 in parallel from the signal conditioner 8 or 14. The output samples 18 or 19 from the A/D converters 90 are preferably communicated to the First-In-First-Out buffers (FIFOs) 91 where they are buffered for distribution to the internal components of the signal detector 10. In the preferred photon measurement system the A/D converters 90 are eight MAX 108 integrated circuits made by Maxim operating at 250 Msample/sec and outputting two data samples at a time in parallel at 125 MHz. The FIFOs 91 are preferably implemented within a Xilinx 4 FPGA. The acquisition synchronizer 92 preferably controls signal acquisition and digital data distribution through the conversion clock (CClk) signals 96.

The acquisition synchronizer 92 is preferably synchronized with an externally provided synchronization clock (SClk) 40 which is also preferably used to synchronize the signal generator 1. The signals CClk[1 . . . N] are preferably generated within the acquisition synchronizer 92 and preferably have the same frequency as SClk 40 but are offset in phase from SClk 40 in N fixed increments of (360/N).degree., with the phase of CClk[1] set to the fixed offset of Z.degree. In the preferred system the internal clock generation capabilities of the Xilinx FPGA are used to implement the acquisition synchronizer 92 directly. The A/D converters 90 preferably perform their conversions in sync with the conversion clocks 96 such that they generate samples at N discrete sample times spread evenly throughout the fundamental sample interval defined by the period of SClk 40. The effective sample rate for the array of converters is preferably N times the rate defined by SClk 40. This process of using multiple A/D converters sampling out of phase to increase the effective sample rate is what we call parallel over-sampling. In the preferred photon measuring system, parallel over-sampling results in an effective sample rate of 2 Gsamples/sec. The offset value Z allows the entire sample set to be offset by some phase from the synchronization clock 40. The acquisition synchronizer 92 preferably is configured such that the value of Z can be varied synchronously with the modulation frame, or with a block of frames called a frame block. This allows Z to follow a sequence of K values smaller than (360/N).degree. such that on successive modulation frames/frame blocks the effective sampling phases (relative to the synchronization clock) take on K values intermediate to those created by the N conversion clocks in any given frame. In this case preferably the input signal at any given A/D converter 90 will be sampled at K discrete phases over K blocks. The detected response 19 is preferably assumed to be stationary with respect to the start of the code pattern block over that time interval. The preferred K discrete sampling phases correspond to K discrete sample times and the effective temporal resolution of the sampling process is preferably increased by a factor of K. This process is referred to as temporal over-sampling.

In the preferred photon measuring system the value of Z is always zero and temporal over-sampling is achieved by adjusting the phase of the modulation as described below rather than by adjusting the phase of the A/D converter sampling. Preferably the FIFOs latch input data to the A/D converters 90 synchronously with the corresponding conversion clock 96. The FIFO 91 output data is preferably provided to the internal components of the signal detector 10 synchronously with the synchronization clock 40 such that all further processing is synchronized with the synchronization clock 40.

Figure 3:
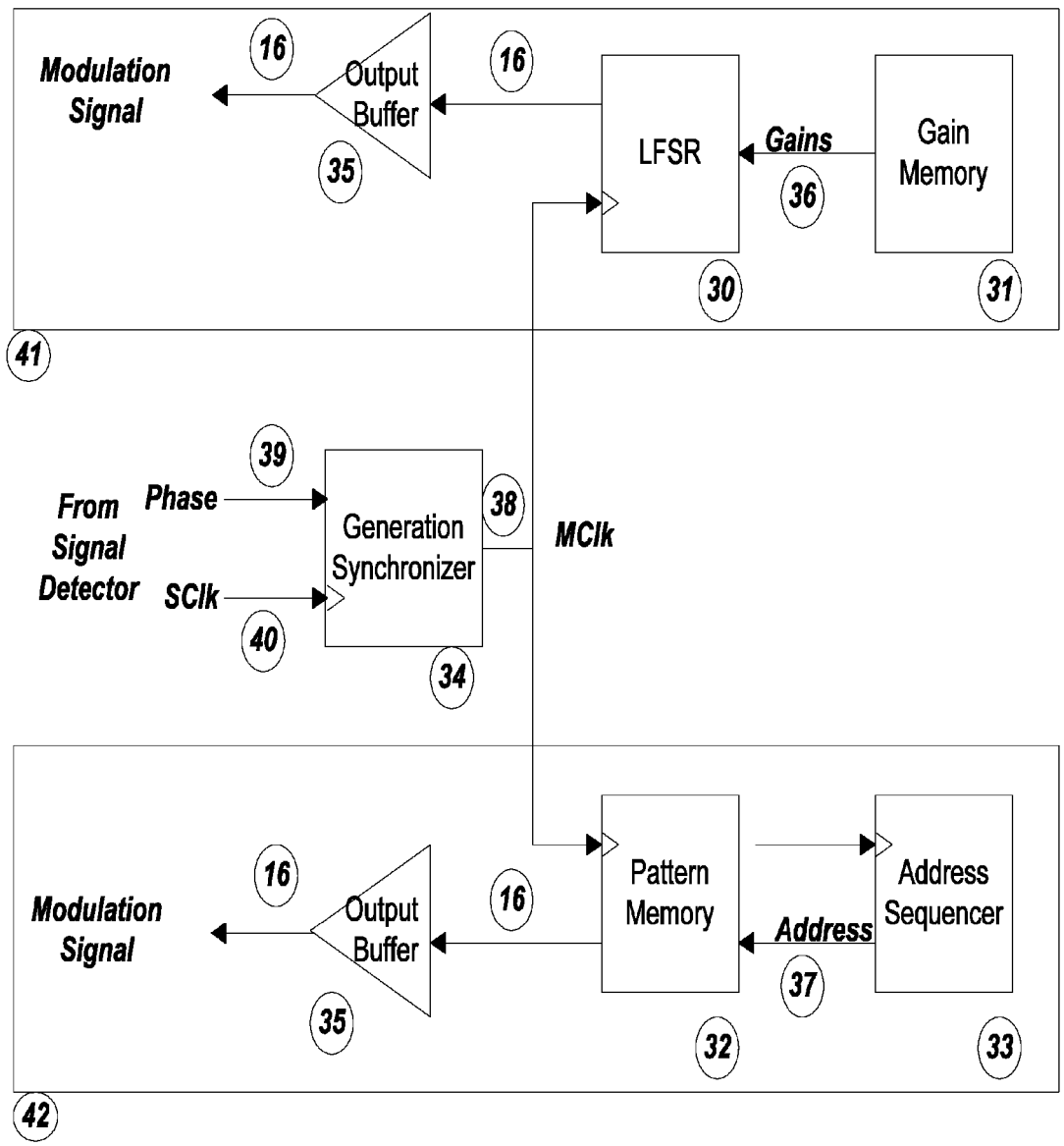
FIG. 3 is a functional block diagram of a preferred signal generator.
Figure 4:
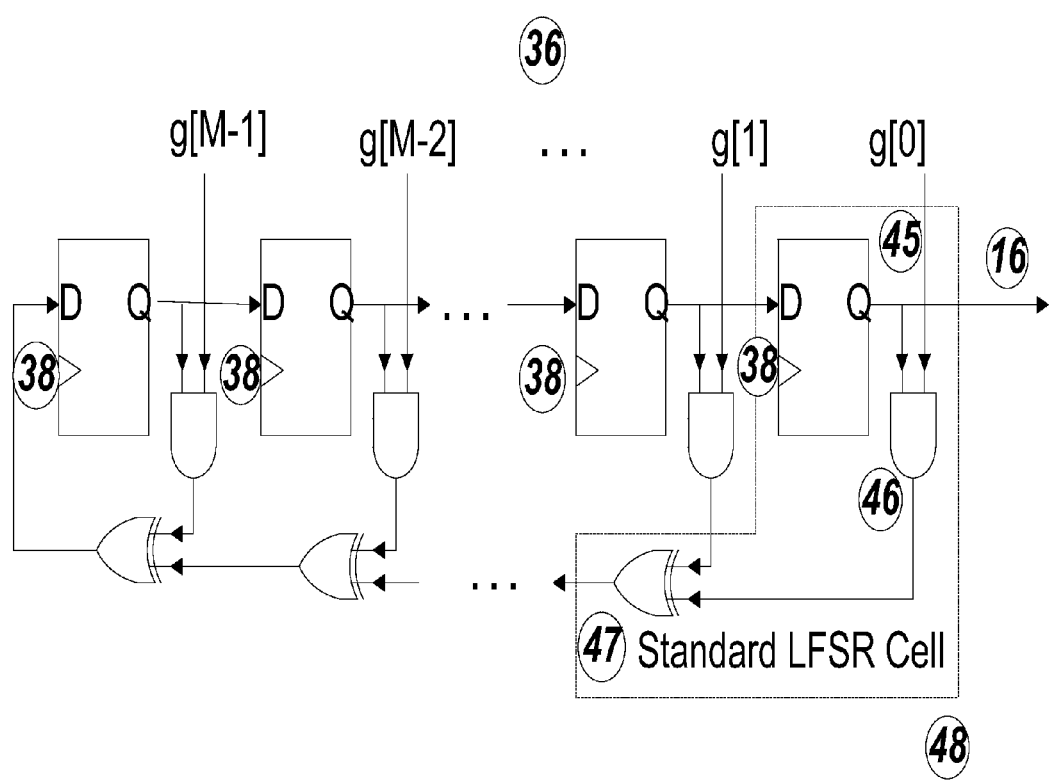
FIG. 4 depicts an implementation of a preferred Linear Feedback Shift Register.
Figure 5:
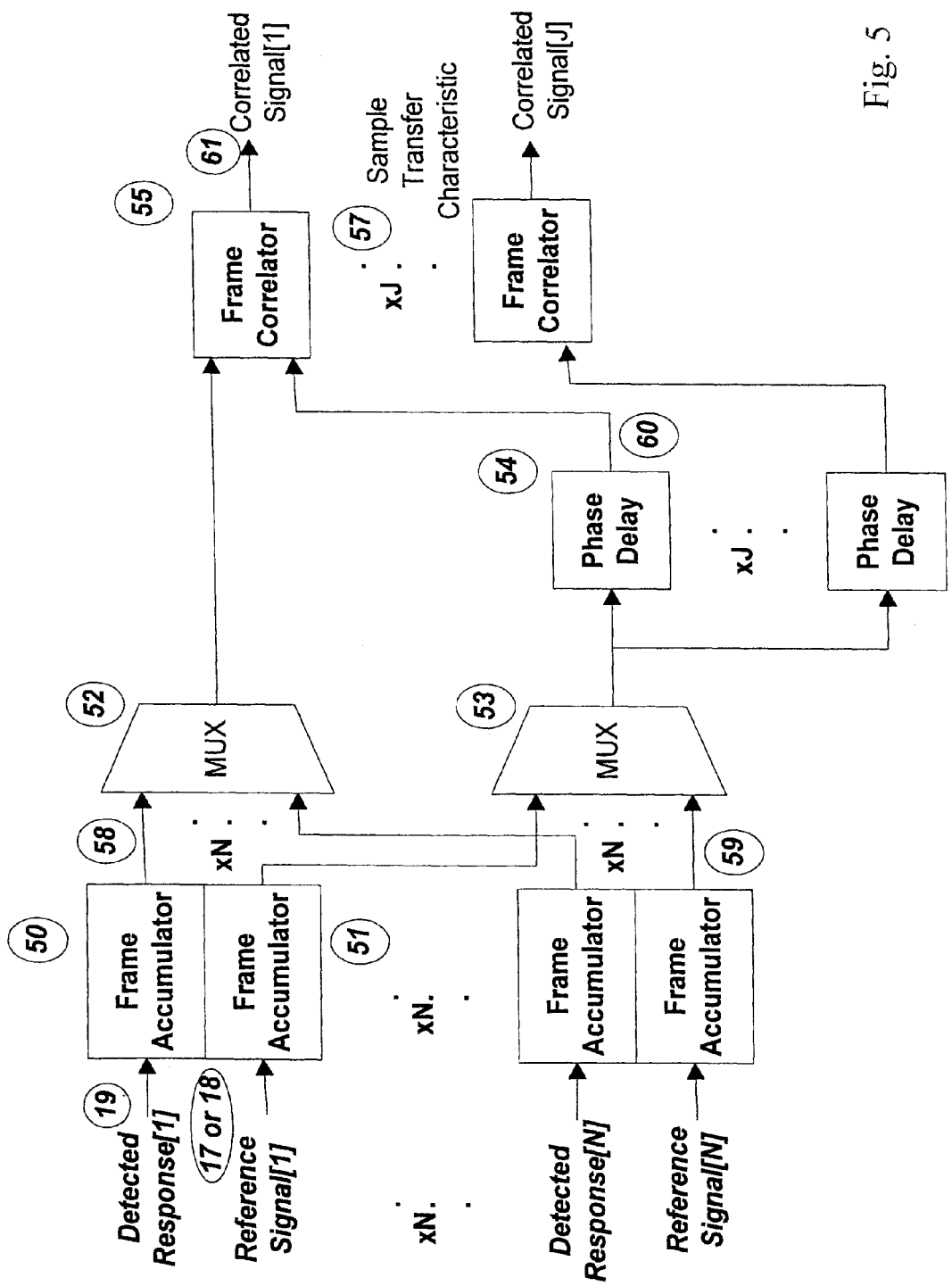
FIG. 5 is a functional block diagram of a preferred signal detector.
Figure 6:
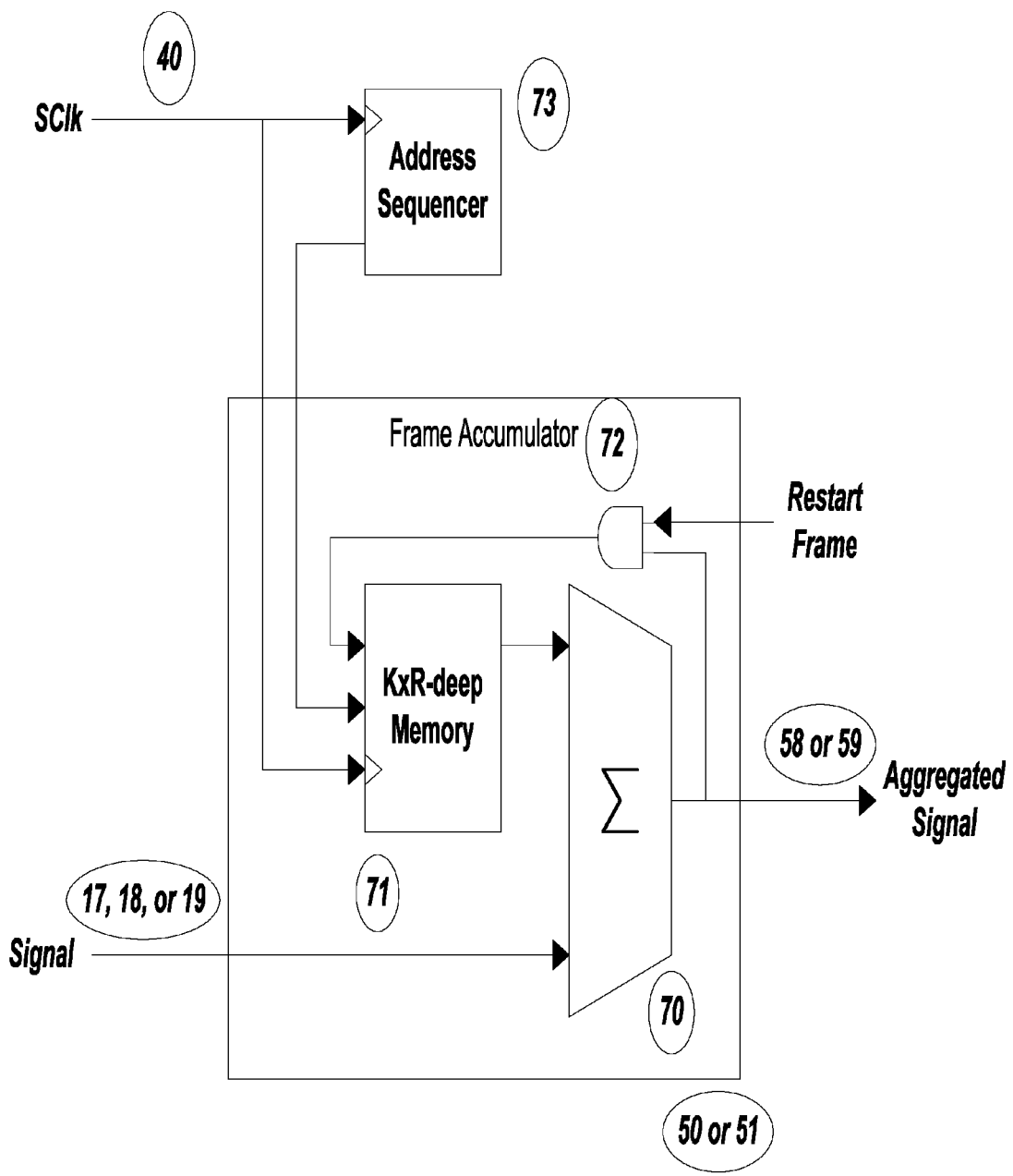
FIG. 6 is a functional block diagram of a preferred frame accumulator.
Figure 7:
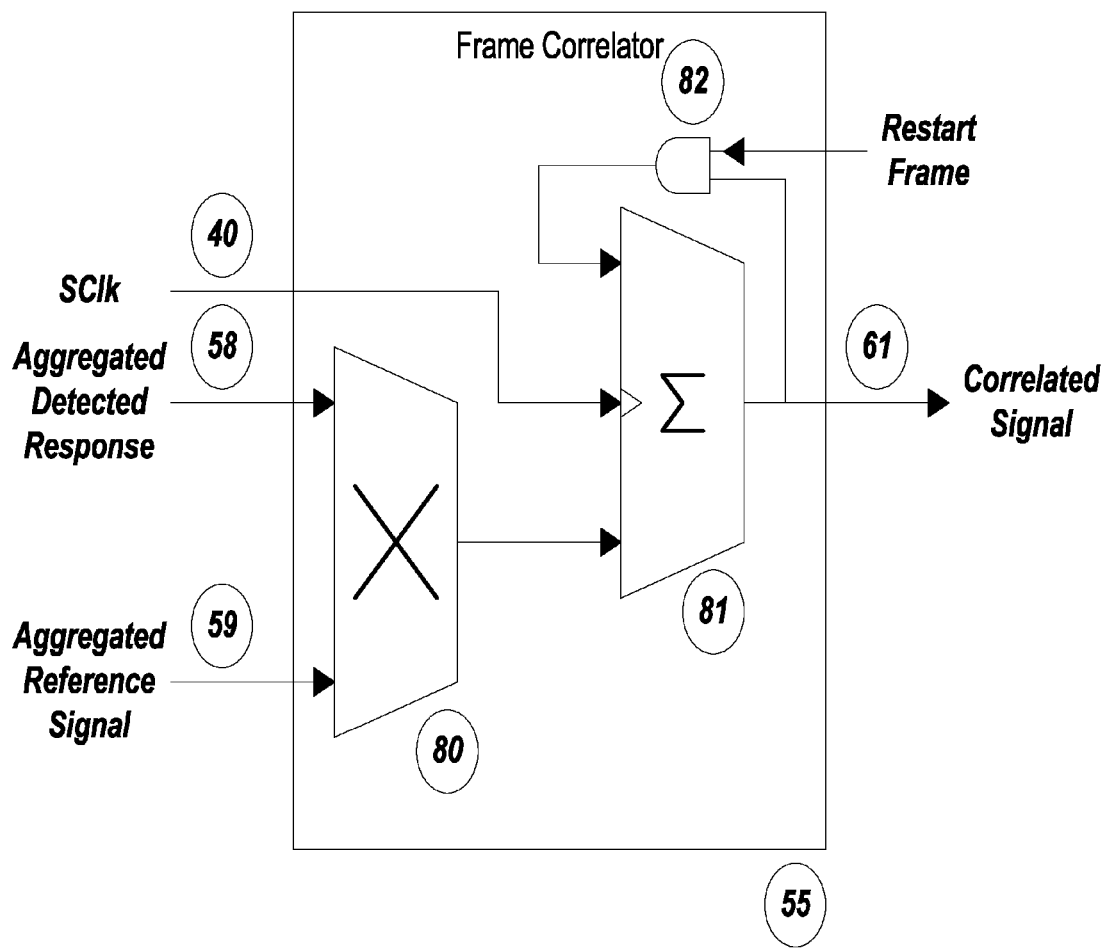
FIG. 7 is a functional block diagram of a preferred frame correlator.

The preferred implementation of the Temporal Response Analysis Engine 11 are shown in FIGS. 3 through 7; the preferred signal generator 1 is shown in FIGS. 3 and 4, while the preferred signal detector 10 is shown in FIGS. 5, 6, and 7.

In the preferred system the Temporal Response Analysis Engine 11 is implemented as logic blocks within a Xilinx 4 FPGA.

The functional blocks of the preferred signal generator 1 are shown in FIG. 3. The top 41 and bottom 42 signal paths are two preferred variants for generating different code patterns for the modulation signal 16. In the top path 41 a Linear Feedback Shift Register (LFSR) 30 is preferably used to create a PRBS code. The specific code pattern is preferably determined by the number of state bits within the LFSR 30 and the gain code 36 input to the LFSR 30. In one preferred implementation the gain code 36 is stored in a gain memory 31, which is preferably configured to allow the code pattern 16 to be changed during operation either by selecting one of several gain codes from a read-only memory or by setting a new gain code into a writable memory. In other embodiments the gain code 36 may be hard-wired into the LFSR 30, or a code-specific state-machine designed to generate a desired code through a series of state transformations may be used in place of the LFSR 30. In the bottom path 42 the entire code pattern is preferably stored as a bit sequence in a pattern memory 32. The sequence in which pattern bits are presented is preferably determined by an address sequencer 33 which preferably provides the cell addresses 37 for the memory. The address sequencer 33 is preferably configured to allow changing the code pattern 16 during operation either by selecting one of several patterns stored in a read-only memory or by inputting a new pattern into a writable memory.

The modulation signal 16 for both the LFSR 30 or pattern memory implementation is preferably buffered by an output buffer 35 to make the signals 16 more robust when driving external components. Timing for presentation of the code pattern bits is preferably controlled by a generation synchronizer 34 which preferably generates the master clock (MClk) 38 for the LFSR 30 and the address sequencer 33. The master clock 38 is preferably synchronized to a system synchronization clock (SClk) 40 which preferably controls both code pattern generation and response signal acquisition. MClk 38 preferably operates at the same frequency as SClk 40 but is preferably offset in phase by an amount specified by the phase input 39, which is preferably an externally programmable parameter. This phase offset allows the relative phase between the modulation signal 16 and the detected response 19 to be adjusted. If the phase is adjusted by some increment, $(360/K)$.degree., at the end of each code pattern block or set of blocks the detected response resulting from the modulation signal will preferably be sampled at K discrete phases over K blocks. In this embodiment of the photon measuring system as with the preferred embodiment, the detected response 19 is assumed to be stationary with respect to the start of the code pattern block over that time interval so that the K discrete sampling phases correspond to K discrete sample times and the effective temporal resolution of the sampling process is increased by a factor of K.

This temporal over-sampling is functionally equivalent to the technique described for temporal over-sampling in the A/D converter embodiment. In other embodiments the external phase specification may represent the phase increment rather than the absolute phase, and the generation synchronizer 34 may increment the phase internally.

The preferred implementation of the LFSR 30 is shown in FIG. 4. The LFSR 30 is preferably a state-machine comprising M standard LFSR cells 48 which hold and transform the state. The LFSR cells 48 are preferably linked in a numbered sequence, and the output from the LFSR 30 is the current state of cell number zero. Each cell preferably comprises a state latch 45 which holds a single bit of state information, a gain element 46 to control the feedback gain for the cell based on the externally provided gain code 36, and an accumulator 47. The accumulator 47 preferably adds the feedback from the cell to the cumulative feedback from all previous cells. At each clock increment the state for a cell is updated to match the previous state from the next higher cell in the chain; the state of the last cell in the chain is updated with the accumulated feedback from all the previous cells. The accumulator 47 for the last cell in the chain may be omitted if desired. The pattern generated by the LFSR 30 is preferably determined by the number of cells in the chain and by the gain code. In a preferred embodiment the gain code is provided from an external source to allow the code pattern to be modified. In other embodiments the gain code may be a fixed value. In embodiments in which the gain code is fixed, the implementation of the gain elements and accumulators for each cell may be optimized for the specific gain code for that cell rather than implemented in the generalized fashion shown. The clock for the LFSR 30 and for all its internal latches is preferably the signal generator master clock 38.

The preferred functional blocks for the signal detector 10 are shown in FIG. 5. The detected response 19 and either the electronic reference signal 17 or the source reference signal 18 are received at two frame accumulators 50 and 51, where the samples for each discrete sample time are accumulated with samples from identical sample times from different modulation frames to form the aggregated detected response 58 and the aggregated reference signal 59. As a result of this aggregation, the effective data rate at which samples are preferably processed in following blocks is reduced by a factor equal to the number of frames aggregated into each sample point. The frame accumulators 50 and 51 are preferably replicated N times to handle the N channels of the A/D converter independently. The internal details of the frame accumulators 50 and 51 for the detected response and the reference signal may differ, depending on the digital format of the two signals. For example, if the reference signal used for analysis is the electronic reference signal 17 rather than the source reference signal 18 its value for each sample time is known a priori to be identical for every frame and to take on only two possible binary values, 0 or 1. In that case preferably the frame accumulator 51 for the reference signal 17 need only store one bit per sample time, equal to the value of the modulation signal for that sample time. At some point between the output of the frame accumulators and final output of the sample transfer characteristic 57 the N acquisition/accumulation channels are preferably re-interleaved into a single data stream. In one preferred embodiment two multiplexers 52 and 53 perform this reintegration at the output of the frame accumulators 50 and 51. In other embodiments this re-integration may take place at any other desired point in the signal processing chain. With or without re-integration the aggregated detected response 58 and the aggregated reference signal 59 are routed to the frame correlator 55 where the two signals 58 and 59 are preferably combined by a cross-correlation algorithm to produce the correlated signal 61 which preferably comprises a single value for each complete aggregated frame of samples. The correlated signal 61 represents the degree to which the aggregated response signal 58 contains components matching the aggregated reference signal 59. If the aggregated reference signal 58 is delayed by a time .tau. before presentation to the correlator 55 then the correlated signal 61 represents the degree to which the aggregated response signal 58 contains components of the delayed version of the reference signal 60. The sample transfer characteristic 57 comprises a set of correlated signals calculated for a range of J such delay times. Phase delay blocks 54 generate the delayed versions of the aggregated reference signal 60. For simplicity the J phase delay blocks 54 are illustrated as discrete components operating in parallel and each providing the complete delay required for one correlated signal. In one preferred embodiment they comprise a cascade of J phase delay blocks each providing the time increment between one correlated signal and the next. The phase delays for the correlated signals are preferably discrete and correspond to integral multiples of the synchronization clock 40 period. The phase delay blocks 54 are preferably implemented as shift registers or FIFOs of the appropriate depth and clocked by the synchronization clock 40. In other embodiments the time delay may be implemented using other methods. In one preferred embodiment each phase delay is processed by a corresponding frame correlator 55. In other embodiments a single frame correlator 55 may be used to calculate the correlated signal 61 for multiple phase delays by presenting the detected response data to its input multiple times, using a different phase delayed version of the reference signal 60 for each iteration. In this case fewer frame correlators 55 are required.

The details of the preferred frame accumulator 50 or 51 are shown in FIG. 6. Samples from the signal 17, 18, or 19 are preferably accumulated in the adder 70 by summing them with values taken from the memory 71; the resulting aggregated signal 58 or 59 is routed to the output of the accumulator and stored back into the memory at the same location from which the original data was taken. Each discrete sample time for the channel is represented by a single addressed cell within the memory. The size of the memory is preferably determined by two parameters, K and R, which preferably encode the sampling scheme. K represents the number of discrete phases at which samples are preferably taken in various frames during temporal over-sampling. R is the ratio of the number of samples in a modulation frame to the number of sampling channels provided in the A/D converter 90 for parallel over-sampling and signifies the number of samples that must be accommodated by each channel within a single frame. A preferred sample enable gate 72 is provided to restart the accumulation process at the beginning of each set of frames by clearing the cells in the memory. The address sequencer 73 selects the cell of the memory to be addressed for each sample point. The frame accumulators 50 or 51 preferably run synchronously with the synchronization clock 40 (although out of phase), so only a single address sequencer is required to address all the frame accumulators.

The details of the preferred frame correlator 55 is shown in FIG. 7. The ideal method for correlating the signals is to take the integral of the detected response 19 weighted by the reference signal 17 or 18. Because the preferred embodiment is a sampled system the integration is approximated by summation over all the samples within a frame set using the adder 81 to generate the correlation signal 61. The weighting of the aggregated detected response 58 by the aggregated reference signal 59 is preferably performed by a multiplier 80. Other embodiments may employ other weighting and integration schemes, including scaling and integration in the analog domain directly on the detected signals. A sample enable gate 82 is preferably provided to restart the accumulation process at the beginning of each set of frames by clearing the correlator.

Figure 8A:
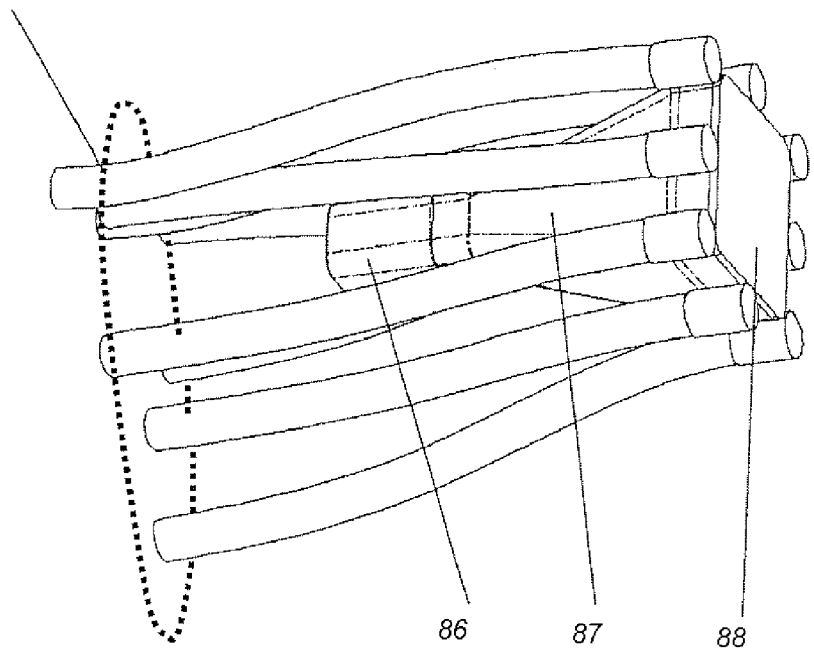
FIGS. 8A and 8B depict an embodiment of the present invention using a 64-element photomultiplier array.
Figure 8B:
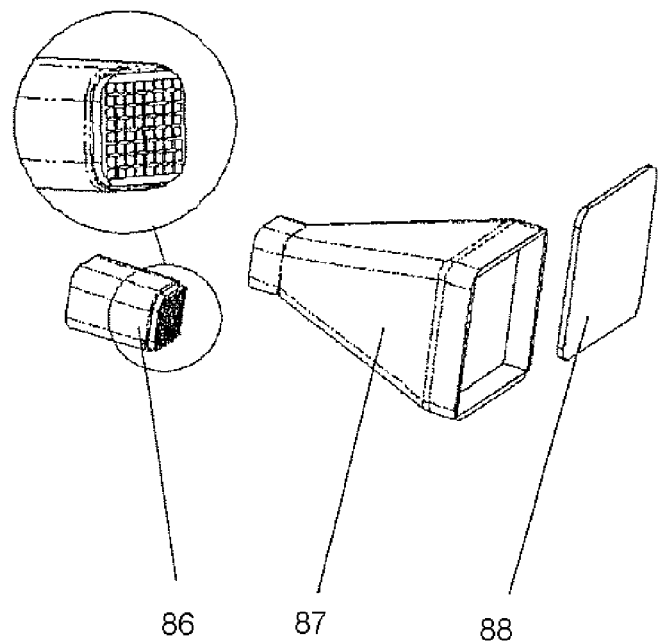
Figure 9:
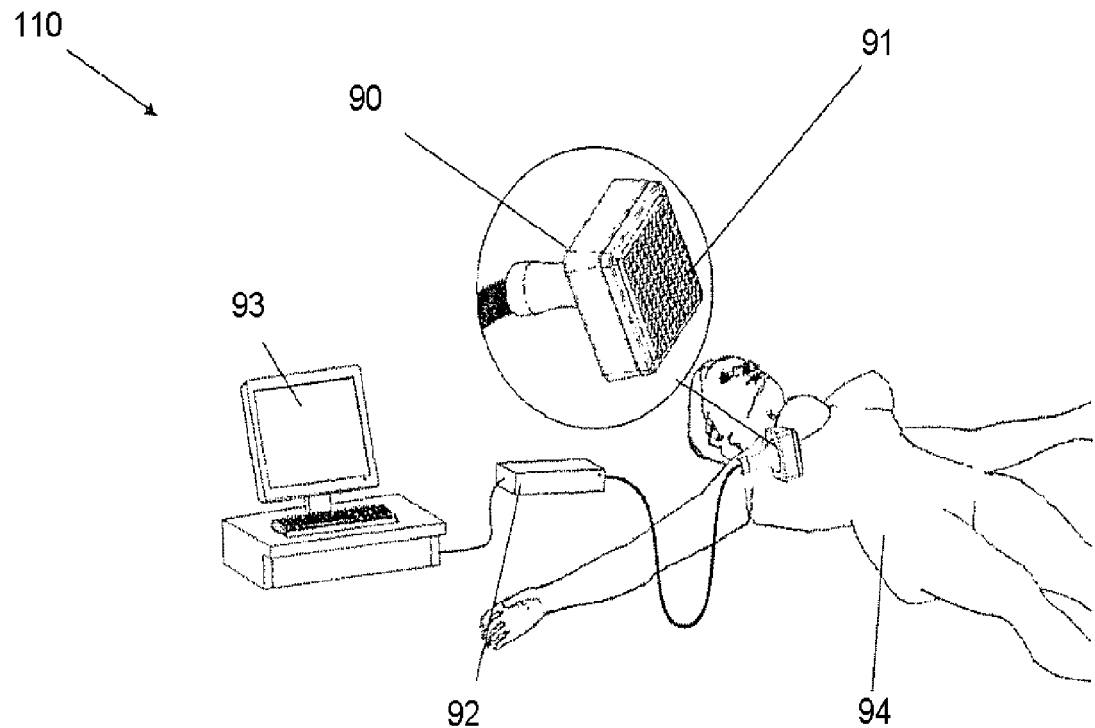
FIG. 9 is an embodiment of the present invention using an 11.times.11 array of fibers to deliver light between the sources or detectors and the patient.

The photon measurement system 100 is useful for interrogating a section of tissue located generally between the light delivery optics and the detection optics. In order to interrogate a larger tissue volume, it is useful to have a system where the photon measurement system is replicated so that separate tissue sections can be interrogated with separate source-detector pairs. One embodiment of such a system is shown in FIGS. 8A and 8B. Eight fiber bundles 85 are used to deliver light from eight different sources to the tissue. The fiber bundles are shown encircled by the dotted line in FIG. 8A. The detectors are a 64-element photomultiplier array 86 manufactured by Hamamatsu with the individual elements in an 8.times.8 arrangement. Fluorescent light from the tissue passes through an optical filter 88 that blocks light at the excitation wavelength. The fluorescent light is coupled to the detector array by a 2.5:1 tapered imaging fiber bundle 87 made by Schott Corp. An exploded view of the detector array 86, filter 88, and imaging fiber bundle 87 is given in FIG. 8B. Each source-detector pair can be coupled to electronics as shown functionally in FIG. 1 to form an individual photon measurement system. Each source-detector pair yields information about photon time of flight through a somewhat different section of tissue than any other pair. Each source can be turned on sequentially, while all the detectors can be sampled simultaneously while a given source is on. Alternatively, each source can be driven with a different code such that any code is orthogonal to the others. In this case, the sources can be driven simultaneously and the low cross-correlation of the respective reference signals allows separation of the signals. The sequential case will exhibit improved signal-to-noise ratio compared to the simultaneously on case due to the non-ideal cross-correlations obtained in practice. Another embodiment of the present invention is shown in FIG. 9. In this case, the imaging instrument 110 includes an 11.times.11 array 91 of multimode fibers for coupling light from the sources and detectors in an electronics module 92 to the tissue. Each fiber can be coupled to either a source or a detector. The fibers are spaced at 1 cm intervals on the imaging head 90. The image reconstructed from the measured data is displayed on the monitor 93. The imaging head 90 can easily be manipulated to image various parts of the patient 94. The present invention is not limited to the particular geometries described here. The use of the photon measurement system 100 is possible with various combinations of sources and detectors and various positions of the sources and detectors. In the examples described, the geometry is a reflection geometry with the sources and detectors effectively on the same side of the tissue. In other embodiments, the detection optics can be placed on the opposite side of the tissue from the light delivery optics. The particular number of sources and detectors can also be varied depending on the resolution and field-of-view required for a particular application. In the present embodiments, the instrument is intended to cover an area of approximately 10 cm.times.10 cm area. Imaging a larger area can be accomplished by moving the instrument head across the area. The embodiments described utilize a photomultiplier array as the optical detectors. In other embodiments, it is possible to use PIN photodiodes, avalanche photodiodes, individual photomultiplier tubes, detector arrays, charge-coupled device arrays, or other photosensitive elements.

The present invention is utilized for sentinel lymph node mapping as presently described. A patient is injected near the site of a malignancy with a dye that fluoresces when exposed to near-infrared light. In particular, indocyanine green (ICG) can be excited at wavelengths around 785 nm and fluoresces at wavelengths around 830 nm. The dye serves both as a visual guide for the surgeon and as a contrast agent for the optical imaging system. ICG has the advantage that it is already approved for use in medical procedures such as angiography; however, several alternative contrast agents are also available. Imaging proceeds as follows. Assuming the imaging is performed reasonably soon after injection of the dye, the dye will be relatively well-localized in the sentinel node or nodes. If the dye is ICG, this amount of time is one the order of minutes. The imaging head is placed in contact or in close proximity to the tissue suspected of containing the sentinel node. The correlator output, or characteristic transfer function, is measured for each source-detector pair. For any given source and detector position, it is possible to calculate a priori the expected characteristic transfer function for a given location of fluorescence dye. In practice, because the tissue is so highly scattering, neighboring source-detector pairs can have somewhat overlapping interrogation regions. The image reconstruction problem consists of estimating the most likely distribution of dye given all the measurements of characteristic transfer functions from all the source-detector combinations. Various techniques are known for performing such an inversion problem, including such methods as singular-value decomposition and the Algebraic Reconstruction Technique, also known as the Gauss-Seidel method. The result of the inversion is a volumetric map of the location of dye within the tissue. Because the dye collects predominantly in the sentinel node(s), this map is effectively a map of the sentinel node location. This map is displayed in the form of an image or images on a monitor attached to the instrument. The surgeon uses this image to plan his surgical incisions. The estimated positions of the sentinel node with respect to the instrument are also displayed on the monitor, allowing the surgeon or other operator to mark the body before the surgery begins.

A preferred imaging method for locating the sentinel lymph node or nodes is as follows. The patient is injected with fluorescent material near the site of a malignancy. Imaging begins after an amount of time sufficient for the fluorescent material to reach the sentinel lymph node or nodes. The instrument head is placed over the patient at a position that represents an initial estimate for the location of the sentinel node. With the instrument head in position, the first optical source is turned on for an amount of time corresponding to the desired number of repeats of the code sequence. Scattered optical waves are measured at each corresponding detector. The output of each detector is correlated with the reference signal as described above to produce a temporal transfer characteristic corresponding to the source-detector combination. The temporal transfer characteristics for each source-detector combination are stored in memory. The process is repeated for each subsequent optical source until temporal transfer characteristics are collected for all desired source-detector pairings. The acquired temporal transfer characteristics are then used to reconstruct an image of the underlying tissue volume using an algorithm implemented in software. The algorithm is based on the ability to estimate a priori the temporal transfer characteristic that will be obtained for any source-detector pairing for any particular location of fluorescent dye. The algorithm generates a most likely estimate of the fluorescent material locations based on the a priori models given the measured temporal transfer characteristics. This estimate of fluorescent material locations is displayed in the form of a volumetric image on a monitor connected to the instrument. The user of the instrument can conclude based on the image whether or not the underlying tissue contains a sentinel node. Generally, the node will be imaged as a subset of the volume with a high estimated concentration of fluorescent material. If the user judges that the sentinel node has been located, he may physically mark the body where the instrument head had been placed with a pen to indicate the area in which to cut. Alternatively, he may save the image on the screen or on a printout so that it may be referred to during surgery. If the user concludes that the sentinel lymph node has not been located, he moves the instrument to a different location and the process is repeated.

Under an embodiment of the present invention, Temporal Response Analysis Engine 11 comprises a general purpose microprocessor. Temporal Response Analysis Engine 11 can also comprise software which provides instructions to the microprocessor. Alternatively, Temporal Response Analysis Engine 11 can comprise an embedded processor or other processor, application specific integrated circuit (ASIC), field programmable gate array (FPGA) or other integrated circuits. Temporal Response Analysis Engine 11 can also comprise firmware.

Under another embodiment of the present invention, the chosen code sequence of digital modulation signal 16 is a unipolar code sequence. Digital modulation signal 16 can be transmitted to optical illumination source 3 or can be used with an external modulator or electro-optic modulator with optical illumination source 3. A unipolar code sequence allows for the use of commercially available continuous wave lasers or light emitting diodes (LEDs) as a light source, for example as optical illumination source 3. A bipolar code sequence does not allow for the use of commercially available continuous wave lasers or LEDs as a light source because a bipolar code sequence requires the transmission of −1's or negative states. With commercially available continuous wave lasers or LEDs, −1's or negative states are difficult to achieve. In addition, the chosen code sequence of digital modulation signal 16 can be a code sequence where the autocorrelation is orthogonal. An orthogonal code sequence can result in a correlation which is flat or relatively flat away from both sides of the peak and can make the processing and analysis for the temporal transfer characteristic or the temporal point spread function easier as well as reducing errors. This characteristic also allows for simultaneous transmission of multiple code sequences and analysis of the multiple code sequences without interference from each code sequence.

Under another embodiment, the chosen code sequence of digital modulation signal 16 is a code sequence with high autocorrelation approaching the delta function and low cross-correlation values. The chosen code sequence can be an Optical Orthogonal Code. Two codes of length N=36 or 36 elements can be used, 110100010000000000000000000000000000 and 100001000000010000000000010000000. The maximum autocorrelation value is 4 and the maximum cross-correlation value is 1. The ratio of the maximum autocorrelation value to maximum cross-correlation value is 4. However, Optical Orthogonal Codes generally have many more 0s (or low states) than 1s (or high states) making them difficult to implement with commercially available continuous wave lasers or LEDs. In addition, the relatively high cross-correlation values hinder the processing and analysis for the temporal transfer characteristic or the temporal point spread function and can introduce errors.

Under another embodiment, the chosen code sequence of digital modulation signal 16 comprises individual code elements where the individual code elements have a length of one nanosecond. Alternatively, individual code element lengths of 25 ps, 50 ps, 75 ps, 100 ps, 125 ps, 150 ps, 175 ps, 200 ps, 250 ps, 500 ps, 750 ps, 1 ns, 1.5 ns, 2 ns, 2.5 ns, 3 ns, 4 ns, 5 ns, 6 ns, 7 ns, 8 ns, 9 ns, 10 ns, 11 ns, 12 ns, 13 ns. 14 ns, 15 ns, 16 ns, 17 ns, 18 ns, 19 ns, 20 ns or any length in between such lengths or any range of lengths in between 25 ps and 20 ns. could be used. Individual code element lengths that are longer allow the use of slower and less expensive lasers or LEDs for optical illumination source 3. However, the amount of time to transmit and process the chosen code sequence of digital modulation signal 16 is dependent on the individual code element lengths multiplied by the number code elements in each sequence. In addition, the width of the temporal transfer characteristic or the temporal point spread function can be as narrow as one nanosecond or less. For narrow temporal transfer characteristics or the temporal point spread functions, a long code element length would lack adequate resolution to properly derive the temporal transfer characteristic or the temporal point spread function.

Under another embodiment, multiple code sequences of 2, 3, 4, 5, 6, 7, 8, 9, 10, 20, 30, 40, 50, 60, 70, 80, 90, 100, 1,000, 10,000, 100,000, 1,000,000 code sequences or any code sequence in between such code sequences or any range of code sequences in between 2 and 1,000,000 code sequences can be used and correlation performed on averaged data or average performed on correlations of data. The multiple code sequences can be multiple identical code sequences. Use of multiple code sequences allows photon measurement system 100 to average out noise effects, improve signal-to-noise ratio, temporary deviations in the system or the sample or average out data prior to stabilization of optical illumination source 3. However, a long individual code element length can result in long processing time particularly for high number of code elements in each sequence and particularly if a large number of multiple code sequences is utilized.

Under another embodiment, the chosen code sequence of digital modulation signal 16 is a code sequence from the Golay class of codes. Golay codes are bipolar making them difficult to use with commercially available continuous wave lasers or LEDs as a light source. However, in this embodiment, the bipolar Golay code sequence is converted into two unipolar code sequences. For example, a bipolar code sequence represented by A(t) can take on values 1 and −1. Two unipolar code sequences UA1(t) and UA2(t) can be constructed where UA1(t)=½[1+A(t)] and UA2(t)=½[1−A(t)].

In addition, complementary Golay codes can be used where the sum of the autocorrelations is a delta function with the maximum autocorrelation value equal to N where N is the length of the code sequence or the number of individual code elements in the code sequence. In this example, the bipolar code sequence represented by A(t) can be converted to two unipolar code sequences UA1(t) and UA2(t) where UA1(t)=½[1+A(t)] and UA2(t)=½[1−A(t)]. The complementary bipolar code sequence represented by B(t) can be converted to two unipolar code sequences UB1(t) and UB2(t) where UB1(t)=½[1+B(t)] and UB2(t)=½[1−B(t)]. Four code sequences UA1(t), UA2(t), UB1(t) and UB2(t) would be used to drive optical illumination source 3. Four readout traces could be obtained RA1(t)=UA1(t)*f(t), RA2(t)=UA2(t)*f(t), RB1(t)=UB1(t)*f(t), and RB2(t)=UB2(t)*f(t). The temporal transfer characteristic or the temporal point spread function can be obtained by performing the following calculation: fest=A(t)·[RA1(t)−RA2(t)]+B(t)·[RA1(t)−RA2(t)]. Using the four unipolar code sequences has the advantage that commercially available continuous wave lasers or LEDs can be utilized as a light source, for example as optical illumination source 3. In addition, the sum of the autocorrelations approaches a delta function where width is related to code element length, making it easier to derive the temporal transfer characteristic or the temporal point spread function. However, using four code sequences has the disadvantage that longer transmission time and longer processing time is required. If optical illumination source 3 is unstable or exhibits amplitude variations or different DC biases, errors can be introduced in processing and processing can be more difficult. In addition, because each code sequence can result in a different DC bias and optical illumination source 3 may require a period of stabilization during each code sequence, the stabilization would introduce additional transmission time and processing time for each code sequence.

Under another embodiment, the chosen code sequence of digital modulation signal 16 is a code sequence from the Galois class of codes. Galois codes do not have ideal autocorrelation but the autocorrelation is uniform on both sides of the peak. The uniformity allows for better or enhanced noise processing and enhanced ability to derive the temporal transfer characteristic and the temporal point spread function. Galois codes have the advantage that it can be implemented with a single unipolar code sequence. The single unipolar code sequence makes photon measurement system 100 less susceptible to instability, amplitude variations or differing DC biases in optical illumination source 3. In addition, to the extent optical illumination source 3 may require a period of stabilization during each code sequence, the stabilization time would have less of an impact on transmission time and processing time. The chosen code sequence of digital modulation signal 16 using a code sequence from the Galois class of codes has a circular autocorrelation of N or approaching N near the peak and −1 or approaching −1 away from the peak, where N is the length of the code sequence or the number of individual code elements in the code sequence. The ratio of the maximum circular autocorrelation value to maximum cross-correlation value is N. A circular code sequence has the important feature that the circular autocorrelation can begin at any point or any code element. The phase of the code sequence does not need to be tracked. The chosen code sequence of digital modulation signal 16 using a code sequence from the Galois class of codes can have 31, 63, 127, 255, 511, 1023, 2047, 4095 and 8191 individual code elements in the code sequence.

Under another embodiment, the chosen code sequence of digital modulation signal 16 is a linear-feedback shift-register sequence, in particular a maximal-length sequence or m-sequence. An n-bit shift register can encode $2^n$ states, so an m-sequence or maximal-length sequence can have $2^{n-1}$ elements before repeating. All zeros in the shift register is a fixed-point unto itself so it cannot be part of any sequence longer than $2^{n-1}$. Maximal-length sequences or m-sequences have one more 1's than 0's. The circular autocorrelation of a maximal-length sequence or m-sequence with itself has one value of $2^{n-1}$ at zero lag and the rest of the values equal to $2^{n-2}$. Although the non-zero value at the other lag is undesirable, it results in a finite transmission of a DC component through the system which can be removed through filtering. A bipolar sequence comprising 1's and −1's can have better autocorrelation. However, −1's require phase sensitive detection.

Under another embodiment, multiple identical code sequences of 2, 3, 4, 5, 6, 7, 8, 9, 10, 20, 30, 40, 50, 60, 70, 80, 90, 100, 1,000, 10,000, 100,000, 1,000,000 code sequences or any code sequence in between such code sequences or any range of code sequences in between 2 and 1,000,000 code sequences can be used. The detected response signal 19 resulting from the entire set of multiple identical code sequences is correlated with the electronic reference signal 17 or source reference signal 18 of the entire set of multiple identical code sequences. The multiple identical code sequences can be periodic or circular. Use of periodic or circular multiple identical code sequences, particularly for Galois class of codes, results in high autocorrelations approaching the delta function and low cross-correlation. This characteristic allows for simultaneous transmission of multiple code sequences and analysis of the multiple code sequences without interference from each code sequence. Each code sequence can be a separate channel and can start at different times. In addition, the autocorrelation of a single code sequence or the correlation of detected response signal 19 resulting from a single code sequence with the electronic reference signal 17 or source reference signal 18 of a single code sequence can result in significant side-lobes. The side-lobes hinder the processing and analysis for the temporal transfer characteristic or the temporal point spread function and can introduce errors. Use of periodic or circular multiple identical code sequences can significantly reduce or eliminate the side-lobes in the autocorrelation or correlation. However, a long individual code element length can result in long processing time particularly for high number of code elements in each sequence and particularly if a large number of multiple code sequences is utilized.

Under another embodiment, radio frequency (RF) shielding is applied to the components of photon measurement system 100. Certain components in photon measurement system 100, for example, signal generator 1, signal conditioner 2, or optical illumination source 3, can generate noise which can appear at optical detector 7, A/D converter 9 or signal detector 10. This noise can then appear in the temporal transfer characteristic or the temporal point spread function making it difficult to analyze or introducing errors for photon time-of-flight, fluorescence lifetime, tissue absorption coefficient, tissue scattering coefficient, location of fluorescing material or other tissue properties or characteristics. Signal generator 1, signal conditioner 2, or optical illumination source 3 can be RF shielded to reduce or avoid noise appearing at optical detector 7, A/D converter 9 or signal detector 10.

Alternatively or concurrently, a delay component or element can be placed between optical illumination source 3 and optical splitter 12A, between optical splitter 12A and optical detector 13, between optical splitter 12B and optical detector 13, between sample 5 and detection optics 6 or between detection optics 6 and optical detector 7. The delay component or element can be a length of free space or a length of optical fiber, optical waveguide or optical bundle. Optical fiber, optical waveguide or optical bundle can be dispersive, both spectral and temporal, can propogate multimodes in the cladding which can distort the optical signal. Free space has the advantage of causing less distortion to the optical signal. A single mirror or 2, 3, 4 or 5 mirrors can be used. Alternatively, retroreflectors, prisms, reflectors or other reflective surface can be used. Use of a reflective surface or a plurality of reflective surfaces allows a given length of free space to occupy significantly less physical dimension and be more compact. A single reflective surface can allow the light to travel back along its original path. In this manner, the physical length can be reduced up to fifty percent. The physical length can be further reduced by using multiple reflective surfaces. With two reflective surfaces, the light can travel along the same path three times, reducing the physical length by up to 66⅔ percent. With three reflective surfaces, the light can travel along the same path four times, reducing the physical length by up to 75 percent. With four reflective surfaces, the light can travel along the same path five times, reducing the physical length by up to 80 percent. With five reflective surfaces, the light can travel along the same path six times, reducing the physical length by up to 83⅓ percent. Alternatively, instead of using three reflective surfaces, two reflective surfaces can be used with the light reflecting off of one reflective surface twice and travelling along the same path four times. Instead of four reflective surfaces, two reflective surfaces can be used with the light reflecting off of each reflective surface twice and travelling along the same path five times. Instead of five reflective surfaces, two reflective surfaces can be used with the light reflecting off of one reflective surface twice and one reflective surface three times, travelling along the same path six times.

The amount of delay resulting from the delay component or element can be adjusted by altering the length or by material selection of materials with differing index of refraction. The delay causes the noise to separate from the temporal transfer characteristic or the temporal point spread function after correlation of detected response signal 19 with the electronic reference signal 17 or source reference signal 18. The separation of noise from the temporal transfer characteristic or the temporal point spread function aides analysis and reduces errors for photon time-of-flight, fluorescence lifetime, tissue absorption coefficient, tissue scattering coefficient, location of fluorescing material or other tissue properties or characteristics. The amount of delay can be 1, 2, 3, 4, 5, 6, 7, 8, 9, 10, 11, 12, 13, 14 or 15 nanoseconds or greater or any delay amount in between such delay amounts or any range of delay amounts in between 1 nanosecond and 15 nanoseconds. A greater amount of delay would require a delay component or element of greater length.

Under another embodiment, photon measurement system 100 is used to measure oximetry in human tissue or more specifically, noninvasive human cerebral oximetry. Photon measurement system 100 can comprise a second optical detector associated with a second optical transmission path from optical illumination source 3 through sample 5. The first optical detector, i.e. optical detector 7, can be associated with a first optical transmission path through sample 5, e.g. through the human scalp and skull only. The second optical detector can be associated with a second optical transmission path e.g. through the human scalp, skull and brain. Tissue characteristics can be derived for the brain alone by comparing the optical signal from the first optical transmission path with the second optical transmission path.

Light attenuation through tissue can be described by the Beer-Lambert law:

$$I = I_0 \exp[-(\mu_a + \mu_s')l]  \quad \text{(Eqn 1)}$$

where I is the measured light intensity after passing through the medium, $I_0$ is the initial light intensity, $\mu_a$ is the absorption coefficient and $\mu_s'$ is the reduced scattering coefficient, and l is the optical path length through the medium. This equation can be rewritten as:

$$-\log\left(\frac{I}{I_o}\right) = \frac{(\mu_a + \mu_s')l}{2.303} = \varepsilon_1 C_1 l + \varepsilon_2 C_2 l + \ldots \varepsilon_n C_n l + \frac{\mu_s' l}{2.303}  \quad \text{(Eqn 2)}$$

where n is the number of absorbing species, $\epsilon$ is the molar absorptivity (also known as the molar extinction coefficient), and C is the concentration of the absorbing species. The absorption coefficient and molar absorptivity are wavelength-dependent and characteristic of a particular molecule. The molar absorptivities for many compounds can be readily determined.

From Eqn 2, the following can be determined:

$$\mu_a = 2.303(\epsilon_1 C_1 + \epsilon_2 C_2 + \ldots \epsilon_n C_n)  \quad \text{(Eqn 3)}$$

In other words, from the absorption coefficient, concentration can be determined without need of optical pathlength. At least n wavelengths of light are required to identify any one absorber of light out of a system of n absorbers.

The primary absorbers in human tissue and blood are oxy-hemoglobin and reduced hemoglobin (also known as deoxyhemoglobin). Water is the next strongest absorber. Therefore, to determine functional oxygen saturation, which is defined as $$O_2 sat \% = \frac{HbO_2}{Hb + HbO_2} \times 100\% \qquad \text{(Eqn 4)}$$

a minimum of 2 wavelengths, preferably 3 to account for the combined effect of water and other absorbers should be used. These 3 wavelengths should fall in the range of 650 nm to 1000 nm, preferably (1) 740 nm to 770 nm, preferably 760 nm; (2) 770 nm to 820 nm, preferably 805 nm (isosbestic point); (3) 820 nm to 1000 nm, preferably 850 nm.

The temporal transfer characteristic or temporal point spread function of the tissue can be extracted from the temporal response profile by using of the Temporal Response Analysis Engine 11. The tissue temporal transfer characteristic or temporal point spread function can be fit with diffusion theory or similar to extract the absorption coefficient, $\mu_a$, independently from the scattering coefficient, optical path length, or other parameters. Alternatively, $\mu_a$ can be found by correlation with other statistical measures of the temporal transfer characteristic or temporal point spread function such as moments of the distribution, peak width at various fractional peak heights, peak area, or by fitting a linear slope to the tail of the profile. Once $\mu_a$ has been determined at each selected wavelength, Eqn 3 can be used to find the concentrations of oxyhemoglobin, deoxyhemoglobin and, if desired, water and other absorbers. The resulting concentrations can then be used in Eqn 4 to calculate oxygen saturation.

Using this technique, the measured concentrations of hemoglobin (and derivatives) can be absolute and accurate, without influence from tissue scattering or variations in optical path length. The oxygen saturation value calculated using these absolute concentrations can also be absolute and accurate.

Photon measurement system 100 can further comprise a second optical illumination source operating at a second wavelength. The first wavelength and second wavelength can be used to determine the amount of oxygenated hemoglobin and deoxygenated hemoglobin. Alternatively, photon measurement system 100 can further comprise a third optical illumination source operating at a third wavelength. The third wavelength can be used to determine the contribution of water or other absorbers to obtain more accurate measurement of oxygenated hemoglobin and deoxygenated hemoglobin. Alternatively, photon measurement system 100 can further comprise a fourth optical illumination source operating at a fourth wavelength. The fourth wavelength can be used to determine the amount of carboxyhemoglobin. Alternatively, photon measurement system 100 can further comprise a fifth optical illumination source operating at a fifth wavelength. The fifth wavelength can be used to determine the amount of methemoglobin. A single optical detector can be used for each wavelength. However, many optical detectors would be required particularly if multiple optical transmission paths are involved. In the example of two wavelengths and two optical transmission paths for each wavelength, four optical detectors would be required. In the example of three wavelength and two optical transmission paths for each wavelength, six optical detectors would be required. However, the difficulty exists of separating and deriving the temporal transfer characteristic or the temporal point spread function for each wavelength since the output signal from the optical detector will represent the combination of multiple wavelengths. In addition, use of multiple detectors can require the use of an optical filter to separate wavelengths, adding loss.

Alternatively, a single optical detector could be used for multiple wavelengths. In the example of two wavelengths and two optical transmission paths, two optical detectors would be required instead of four. In the example of three wavelengths and two optical transmission paths, two optical detectors would be required instead of six. In addition, it can still present difficulties especially if wavelengths are close in spectrum to each other resulting in incomplete separation. Photon measurement system 100 or Temporal Response Analysis Engine 11 can further comprise a separate signal generator for a wavelength or an optical illumination source. The timing of the initiation of the chosen code sequence of the digital modulation signal for multiple signal generators can be delayed. The initiation delay can cause the temporal transfer characteristic or the temporal point spread function for the associated wavelength or associated optical illumination source to be delayed with respect to another wavelength or optical illumination source. This delay can result in separation of the temporal transfer characteristic or the temporal point spread function for individual wavelengths making it easier to distinguish the temporal transfer characteristic or the temporal point spread function for individual wavelengths. Alternatively, the same result can be achieved by using different code sequence for separate signal generators. Code sequence could be chosen that result in separation or delay of the temporal transfer characteristic or the temporal point spread function for different wavelengths. The separation or delay can also be implemented by placing a delay component or element between optical illumination source 3 and optical splitter 12A, between optical splitter 12A and optical detector 13, between optical splitter 12B and optical detector 13, between sample 5 and detection optics 6 or between detection optics 6 and optical detector 7. The delay component or element can be a length of free space or a length of optical fiber, optical waveguide or optical bundle.

The separation or delay can be characterized in terms of time or number of code elements. The amount of time for the separation or delay can be calculated as the number of code elements for the separation or delay multiplied by the length of the individual code element. The separation or delay can also be characterized in terms of fractions or percentage of the number of individual code elements in each code sequence. The amount of separation or delay can be set by starting the code sequence at a different point for each wavelength. As an example, if two wavelengths are used with a code sequence of 31 individual elements and individual code element length of 1 nanosecond, the first wavelength could be transmitted starting with the first code element and the second wavelength could be transmitted starting with the $15^{th}$ or $16^{th}$ code element. The amount of separation or delay between the first wavelength and second wavelength in this example would be 14 nanoseconds and 15 nanoseconds for transmission starting with $15^{th}$ and $16^{th}$ code element, respectively. Starting the second wavelength at the $15^{th}$ or $16^{th}$ code element provides maximum amount of separation or delay between first wavelength for code sequence of 31 individual elements. Increased amount of separation or delay allows the temporal transfer characteristic or the temporal point spread function for different wavelengths to be more easily distinguished from one another. For code sequence of 63 individual elements, starting the second wavelength at the $31^{st}$ or $32^{nd}$ code element provides maximum amount of separation or delay between the first wavelength. For code sequence of 127 individual elements, starting the second wavelength at the $63^{rd}$ or $64^{th}$ code element provides maximum amount of separation or delay between the first wavelength. For code sequence of 255 individual elements, starting the second wavelength at the $127^{th}$ or $128^{th}$ code element provides maximum amount of separation or delay between the first wavelength. For code sequence of 511 individual elements, starting the second wavelength at the $255^{th}$ or $256^{th}$ code element provides maximum amount of separation or delay between the first wavelength. For code sequence of 1023 individual elements, starting the second wavelength at the $511^{st}$ or $512^{nd}$ code element provides maximum amount of separation or delay between the first wavelength. For code sequence of 2047 individual elements, starting the second wavelength at the $1023^{rd}$ or $1024^{th}$ code element provides maximum amount of separation or delay between the first wavelength. For code sequence of 4095 individual elements, starting the second wavelength at the $2047^{th}$ or $2048^{th}$ code element provides maximum amount of separation or delay between the first wavelength. For code sequence of 8191 individual elements, starting the second wavelength at the $4095^{th}$ or $4096^{th}$ code element provides maximum amount of separation or delay between the first wavelength. Alternatively, for each of the code sequences of 31, 63, 127, 255, 511, 1023, 2047, 4095 and 8191 individual elements described, the second wavelength can start at the code element representing 25, 26, 27, 28, 29, 30, 31, 32, 33, 34, 35, 36, 37, 38, 39, 40, 41, 42, 43, 44, 45, 46, 47, 48 or 49 percent of the total number of individual elements in the code sequence or any percentage in between such percentages or any range of percentages in between 25 percent and 49 percent. Alternatively, for each of the code sequences of 31, 63, 127, 255, 511, 1023, 2047, 4095 and 8191 individual elements described, the second wavelength can start at the code element representing 51, 52, 53, 54, 55, 56, 57, 58, 59, 60, 61, 62, 63, 64, 65, 66, 67, 68, 69, 70, 71, 72, 73, 74 or 75 percent of the total number of individual elements in the code sequence or any percentage in between such percentages or any range of percentages in between 51 percent and 75 percent.

If three wavelengths are used with a code sequence of 31 individual elements and individual code element length of 1 nanosecond, the first wavelength could be transmitted starting with the first code element, the second wavelength could be transmitted starting with the $10^{th}$ or $11^{th}$ code element and the third wavelength could be transmitted starting with the $20^{th}$ or $21^{st}$ code element. The amount of separation or delay between the first wavelength and second wavelength in this example would be 9 nanoseconds and 10 nanoseconds for transmission starting with $10^{th}$ and $11^{th}$ code element, respectively. Starting the second wavelength at the $10^{th}$ or $11^{th}$ code element and the third wavelength at the $20^{th}$ or $21^{st}$ code element provides maximum amount of separation or delay between wavelengths for code sequence of 31 individual elements. For code sequence of 63 individual elements, starting the second wavelength at the $21^{st}$ code element and the third wavelength at the $42^{nd}$ code element provides maximum amount of separation or delay between wavelengths. For code sequence of 127 individual elements, starting the second wavelength at the $42^{nd}$ or $43^{rd}$ code element and the third wavelength at the $84^{th}$ or $85^{th}$ code element provides maximum amount of separation or delay between wavelengths. For code sequence of 255 individual elements, starting the second wavelength at the $85^{th}$ code element and the third wavelength at the $170^{th}$ code element provides maximum amount of separation or delay between wavelengths. For code sequence of 511 individual elements, starting the second wavelength at the $170^{th}$ or $171^{st}$ code element and the third wavelength at the $340^{th}$ or $341^{st}$ code element provides maximum amount of separation or delay between wavelengths. For code sequence of 1023 individual elements, starting the second wavelength at the $341^{st}$ code element and the third wavelength at the $682^{nd}$ code element provides maximum amount of separation or delay between wavelengths. For code sequence of 2047 individual elements, starting the second wavelength at the $682^{nd}$ or $683^{rd}$ code element and the third wavelength at the $1364^{th}$ or $1365^{th}$ code element provides maximum amount of separation or delay between the first wavelength. For code sequence of 4095 individual elements, starting the second wavelength at the $1365^{th}$ and the third wavelength at the $2730^{th}$ code element provides maximum amount of separation or delay between wavelengths. For code sequence of 8191 individual elements, starting the second wavelength at the $2730^{th}$ or $2731^{st}$ code element and the third wavelength at the $5460^{th}$ or $5461^{st}$ code element provides maximum amount of separation or delay between wavelengths. Alternatively, for each of the code sequences of 31, 63, 127, 255, 511, 1023, 2047, 4095 and 8191 individual elements described, the second wavelength can start at the code element representing 17, 18, 19, 20, 21, 22, 23, 24, 25, 26, 27, 28, 29, 30, 31, 32 or 33 percent of the total number of individual elements in the code sequence or any percentage in between such percentages or any range of percentages in between 17 percent and 33 percent. Alternatively, for each of the code sequences of 31, 63, 127, 255, 511, 1023, 2047, 4095 and 8191 individual elements described, the second wavelength can start at the code element representing 34, 35, 36, 37, 38, 39, 40, 41, 42, 43, 44, 45, 46, 47, 48, 49 or 50 percent of the total number of individual elements in the code sequence or any percentage in between such percentages or any range of percentages in between 34 percent and 50 percent. Alternatively, for each of the code sequences of 31, 63, 127, 255, 511, 1023, 2047, 4095 and 8191 individual elements described, the third wavelength can start at the code element representing 51, 52, 53, 54, 55, 56, 57, 58, 59, 60, 61, 62, 63, 64, 65 or 66 percent of the total number of individual elements in the code sequence or any percentage in between such percentages or any range of percentages in between 51 percent and 66 percent. Alternatively, for each of the code sequences of 31, 63, 127, 255, 511, 1023, 2047, 4095 and 8191 individual elements described, the third wavelength can start at the code element representing 67, 68, 69, 70, 71, 72, 73, 74, 75, 76, 77, 78, 79, 80, 81, 82 or 83 percent of the total number of individual elements in the code sequence or any percentage in between such percentages or any range of percentages in between 67 percent and 83 percent.

Figure 10:
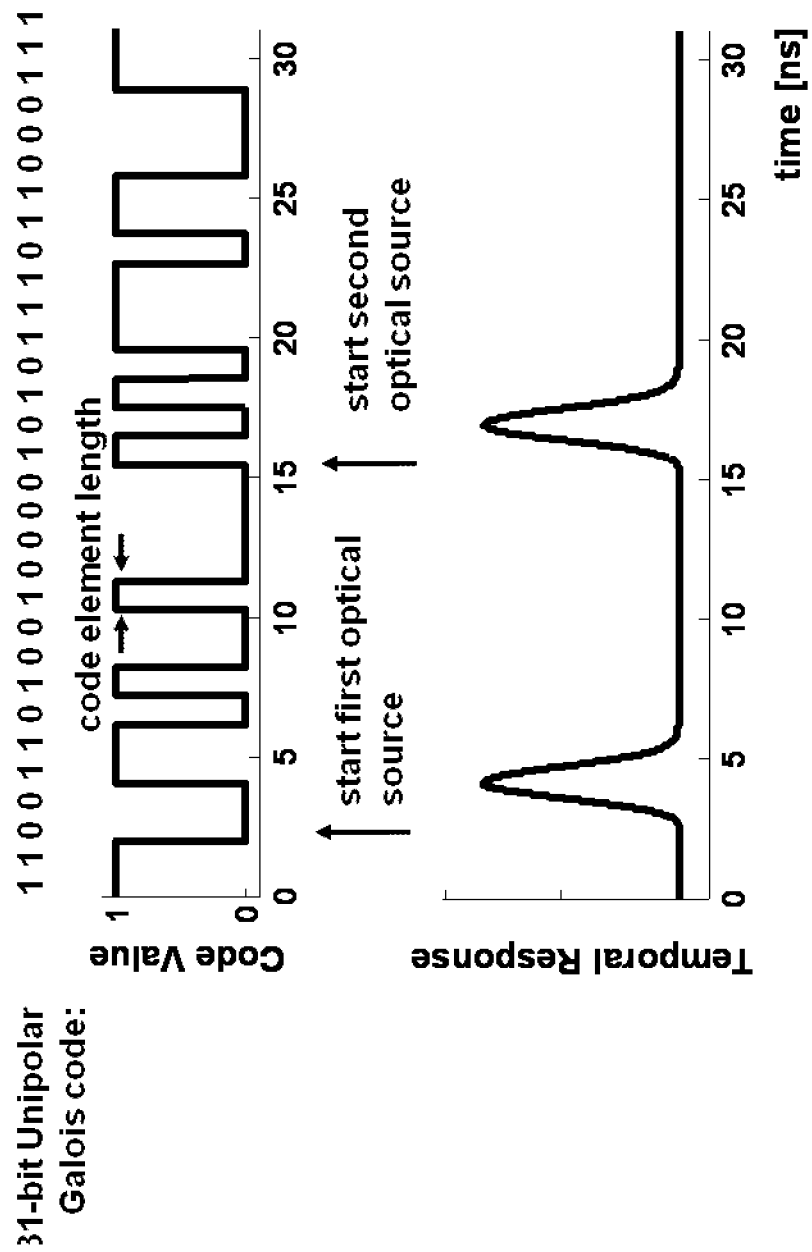
FIG. 10 is a diagram illustrating the use of a 31-bit unipolar Galois code in one embodiment of the present invention.

FIG. 10 is a diagram illustrating the use of a 31-bit unipolar Galois code in one embodiment of the present invention. The chosen code sequence of digital modulation signal 16 is 1100110010000101011101100011111 and starts with the third element or 0011010010000101011101100011111. The code sequence has 31 individual code elements and is unipolar. It is also a Galois code sequence. FIG. 10 also illustrates the resulting digital modulation signal 16 after using the chosen 0011010010000101011101100011111 sequence and illustrates a code element length of 1 nanosecond. The chosen 0011010010000101011101100011111 sequence is used on the first optical illumination source at the first wavelength and the second optical illumination source at the second wavelength in a circular or repeating manner i.e. multiple code sequences are used. The chosen 0011010010000101011101100011111 sequence is used in a circular or repeating manner with the first optical illumination source at the first wavelength starting with the third element. After 13 nanoseconds, the chosen 0011010010000101011101100011111 sequence is used in a circular or repeating manner with the second optical illumination source at the second wavelength. Alternatively, both optical illumination sources can be started at the same time. A chosen 00110100100001010111011000111111 sequence is used in a circular or repeating manner with the first optical illumination source at the first wavelength. A second version of the same chosen sequence beginning at the sixteen element is used in a circular or repeating manner with the second optical illumination source at the second wavelength. The second version of the same chosen sequence is 10101110110001111100110100100000. FIG. 10 also illustrates the resulting temporal transfer characteristic or the temporal point spread function of this example. A delay exists between the peaks of the temporal transfer characteristic or the temporal point spread function of the first wavelength and second wavelength.

Under another embodiment, Temporal Response Analysis Engine 11 analyzes and processes the correlation of detected response signal 19 with the electronic reference signal 17 or source reference signal 18. The correlation contains both the instrument response function and the temporal transfer characteristic or the temporal point spread function. Temporal Response Analysis Engine 11 derives or separates the instrument response function from the temporal transfer characteristic or the temporal point spread function in the correlation. The temporal transfer characteristic or the temporal point spread function can change over time based on changes in properties or characteristics of sample 5 over time, particularly if sample 5 is live human tissue. However, the instrument response function can be less susceptible to change over time depending on the stability of the hardware or equipment. Temporal Response Analysis Engine 11 can measure the instrument response function independently without the temporal transfer characteristic or the temporal point spread function by implementing a calibration procedure where the instrument response function is measured while sample 5 is removed from the optical path between optical illumination source 3 and optical detector 7. This removal can be accomplished by physically removing sample 5 or altering the optical transmission path between sample 5 and optical detector 7 to avoid sample 5. Once the instrument response function is determined, the temporal transfer characteristic or the temporal point spread function can be derived from the correlation of detected response signal 19 with the electronic reference signal 17 or source reference signal 18.

Alternatively, the instrument response function can be approximated without independent or direct measurement. By avoiding independent or direct measurement, the calibration procedure is avoided. In addition, when photon measurement system 100 is operating for a longer period of time, re-calibration may be required if photon measurement system 100 drifts. By avoiding independent or direct measurement, re-calibration is also avoided. The instrument response function is assumed to be fixed or constant over time or varying slowly over time. Temporal Response Analysis Engine 11 first obtains or stores a set of correlations of detected response signal 19 with the electronic reference signal 17 or source reference signal 18. Each correlation can result from a single code sequence, multiple code sequences or multiple identical code sequences. Each correlation is associated with a given point in time. The set of correlations can comprise 20 correlations or 4, 5, 6, 7, 8, 9, 10, 11, 12, 13, 14, 15, 16, 17, 18, 19, 25, 50, 75, 100, 150, 200, 250, 300, 350, 400, 450, 500 or any number in between such numbers or any range of correlations in between 4 and 500. Temporal Response Analysis Engine 11 initially selects one of the correlations from the set of correlations which can be the first correlation. The selected correlation can initially be assumed to be or treated as the instrument response function.

Temporal Response Analysis Engine 11 generates a set of temporal transfer characteristics or the temporal point spread functions associated with a range of photon times-of-flight, fluorescence lifetimes, tissue absorption coefficients, tissue scattering coefficients, location of fluorescing material or other tissue properties or characteristics, either prior to or after selection of the selected correlation. For noninvasive human cerebral oximetry, Temporal Response Analysis Engine 11 generates a set of temporal transfer characteristics or the temporal point spread functions associated with a range of oxygenated and deoxygenated hemoglobin levels.

Temporal Response Analysis Engine 11 convolves the set of temporal transfer characteristics or the temporal point spread functions with the selected correlation resulting in a set of convolutions. The set of convolutions is compared with the set of correlations using the least squared method and the difference recorded or stored. Temporal Response Analysis Engine 11 then modifies the selected correlation or assumed instrument response function and convolves the set of temporal transfer characteristics or the temporal point spread functions with the modified correlation resulting in a set of modified convolutions. The set of modified convolutions is compared with the set of correlations using the least squared method and the difference recorded or stored. Temporal Response Analysis Engine 11 repeats the steps or process for different modified or assumed instrument response functions iteratively until the difference between the set of modified convolution and the set of correlations is minimized under the least squared function analysis. The modified convolution or assumed instrument response function that results in the minimal difference between the set of convolutions and the set of correlations is treated as or assumed to be the actual instrument response function. The temporal transfer characteristic or the temporal point spread function is separated from the instrument response function and then used as described to obtain $\mu_a$ and the concentrations of interest.

Figure 11:
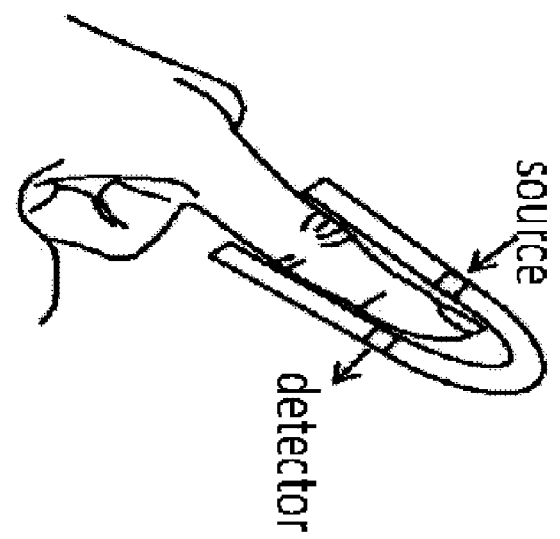
FIG. 11 is a diagram illustrating the placement of source and detector to measure total hemoglobin under one embodiment of the present invention.
Figure 11:
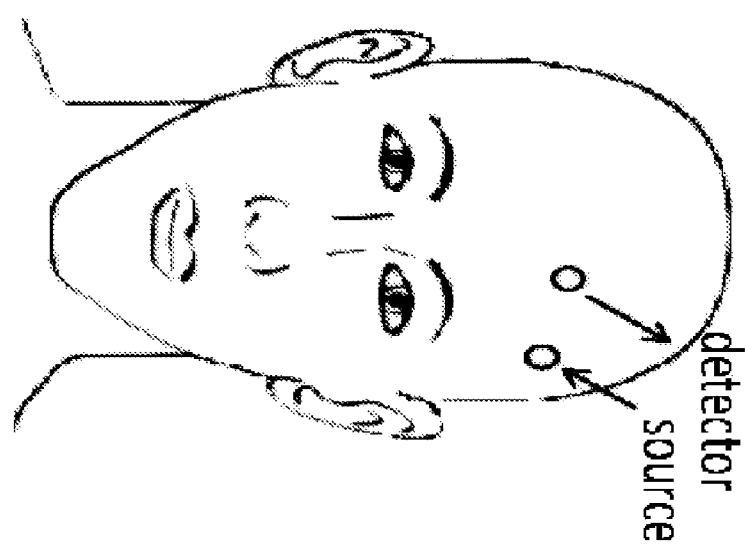

FIG. 11 is a diagram illustrating the placement of source and detector to measure total hemoglobin under one embodiment of the present invention. Under this embodiment, photon measurement system 100 is used to measure total hemoglobin level in human tissue. Total hemoglobin is an important parameter that can be used to guide many clinical interventions. It is the sum of the concentrations of oxyhemoglobin, reduced (or deoxy-) hemoglobin, carboxyhemoglobin, and methemoglobin An approximation can be utilized to use only oxygemoglobin and reduced hemoglobin to calculate total hemoglobin; this approximation is robust in healthy individuals.

Total hemoglobin can be also essential to the accurate calculation of blood oxygen saturation. Fractional oxygen saturation can be determined by dividing the concentration of oxyhemoglobin by the concentration of total hemoglobin. If only oxyhemoglobin plus reduced hemoglobin is used to calculate total hemoglobin, the resulting oxygen saturation can be defined as functional oxygen saturation.

Accurate measurement of total hemoglobin can be vital, yet the majority of point-of-care hemometry devices actually measure hematocrit and apply an assumption of hemoglobin content per cell to calculate hemoglobin. Hematocrit is the percentage of red blood cells in whole blood. To convert from hematocrit to hemoglobin, the mean corpuscular hemoglobin concentration must be known. This value ranges from 32 to 36 g/dL in normal individuals.

Hematocrit can be measured in many blood gas analyzers by conductimetry. This technique is based on the principle that plasma is rich in electrolytes and is highly conductive, whereas blood cells are non-conductive. Thus, the greater the electrical conduction, the fewer the cells. While this technique can be fairly robust under normal physiological conditions, many illnesses and therapies can cause erroneous readings. Fluid resuscitation, for example, can produce significant hemodilution with hyperosmolar solutions. The injection of radiographic contrast media, which has very high osmolarity, can greatly increase conduction while not significantly diluting the blood. Some protocols can include the administration of proteins, such as albumin, which are similar to blood cells in that they are non-conductive. As a result, conductimetric readings can be very inaccurate and can adversely impact the course of treatment for a patient.

Other point-of-care devices can extract a small volume of blood from a fingerprick to measure hematocrit. However, the process of applying pressure to the capillary bed can result in a different proportion of plasma to extracted red blood cells as exists in the vessels.

One spectrophotometry system has the potential to accurately measure hemoglobin itself without need for assumptions or calculations and is not adversely affected by hemodilution or hyperosmolar solutions. The challenges of using such spectrophotometry to measure hemoglobin include contributions from other skin chromophores, variations in blood vessel location and density, and changes in vessel diameter and subsequent optical path length during pulsation. Measurement of arterial diameter or pulsatile path length is a prerequisite for accurate noninvasive determination of hemoglobin concentration with such spectrophotometry.

The total hemoglobin system of one embodiment of the present invention mitigates the problems encountered by other methods and provides an accurate measure of hemoglobin concentration, with inherent optical pathlength correction. Modulated light at two to four or more wavelengths using a pseudo-random sequence is detected either in transmission mode, such as through a finger or earlobe, or in reflection mode, such as through the forearm, temple, neck, or other suitable location. The detected light contains the temporal response of the sample, which may be fit using diffusion theory or similar techniques to obtain the absorption coefficient, the scattering coefficient, and the optical path length independently. The absorption coefficient, $\mu_a$, is related to concentration by $\mu_a = 2.303(\epsilon_1 + \epsilon_2 + \ldots \epsilon_n C_n)$ where n is the number of absorbing species present in the sample, e is the wavelength-dependent molar absorption coefficient (a known constant), and C is the concentration. Hemoglobin is the primary absorbing species in blood and tissue. To determine the concentrations of oxyhemoglobin and reduced hemoglobin, measurements at two wavelengths can be used to isolate each contribution. Alternatively, a single measurement at the isosbestic point for the two species, 805 nm wavelength, can give the combined concentration, i.e. total hemoglobin under the approximation that oxy- and reduced hemoglobin dominate. For a more accurate measurement, additional measurements at additional wavelengths can be included to account for other absorbing species. It is not necessary to add wavelengths to account for scatter. To determine the concentrations of all four of the primary forms of hemoglobin, oxyhemoglobin, reduced hemoglobin, carboxyhemoglobin, and methemoglobin, measurements at a minimum of four wavelengths can be used to isolate each contribution.

Wavelengths used can be in the range of 650 nm to 1000 nm preferably 850 nm, 805 nm (isosbestic point of oxy- and reduced hemoglobin), 780 nm (isosbestic point of reduced hemoglobin and methemoglobin), 760 nm, 660 nm (isosbestic point of reduced hemoglobin and methemoglobin), and 630 nm. Additional wavelengths can be added to compensate for water absorption and, if desired, bilirubin absorption. The preferred wavelengths for bilirubin absorption is 400-500 nm, more specifically 450 nm.

The absorption coefficient obtained by transmission or reflection measurement through at least in part a blood vessel, can also include contributions from surrounding tissue, capillary beds, and venous blood. To obtain the absorption coefficient due solely to arterial hemoglobin, measurements can be acquired at systole and diastole and the resulting absorption coefficients subtracted from one another to remove unwanted contributions. Using multiple wavelengths as described, hemoglobin concentration can be determined from absorption coefficients. It is desirable to measure at least twice during systole and twice during diastole or 3, 4 or 5 times during systole and diastole, preferably 6, 7, 8, 9 or 10 times during systole and diastole. Additionally, a trigger could be utilized to trigger measurement during the lowest pressure of diastole and highest pressure of systole. Photon measurement system 100 can be used to take measurements during systole and diastole with heart rates of 60 to 100 beats per minute and up to 220 beats per minute. With a heart rate of 60 beats per minute and two measurements for systole and diastole, photon measurement system 100 would take a minimum of four measurements per second or measure at a rate of 0.25 seconds per measurement. The code sequence utilized would not exceed 0.25 seconds. With a heart rate of 220 beats per minute and 10 measurements for systole and diastole, photon measurement system 100 would take a minimum of 73⅓ measurements per second or measure at a rate of 0.0136 seconds per measurement. The code sequence utilized would not exceed 0.0136 seconds. Photon measurement system 100 can take measurements at a rate of 4, 5, 6, 7, 8, 9, 10, 15, 20, 30, 40, 50, 60, 70 or 73⅓ measurements per second or any rate in between such rates or any range of rate in between 4 and 73⅓ measurements per second. Photon measurement system 100 can measure at a rate of 0.0136, 0.015, 0.0175, 0.02, 0.03, 0.04, 0.05, 0.075, 0.1, 0.125, 0.15, 0.2, 0.25 seconds per measurement or any rate in between such rates or any range of rate in between 0.0136 and 0.25 seconds per measurement. Prior systems utilizing short-pulsed lasers and single photon counting detectors are not sufficiently fast to make enough measurements during the heartbeat cycle. On the other hand, photon measurement system 100 can derive the temporal transfer characteristic or the temporal point spread function and determine absorption coefficients or hemoglobin levels with a single code sequence providing the capability to make measurements at the rates described.

Alternatively, the source or plurality of sources and the detector or plurality of detectors can be aligned over a blood vessel or capillary bed such as an artery near the temple with the source or plurality of sources and the detector or plurality of detectors spaced apart approximately twice the distance that the artery is deep. This alignment ensures the photon path travels at least in part through the artery. Depth discrimination can be possible utilizing time-domain information. Photons that have traveled longer paths have longer arrival times.

When measuring vessels near the surface, external temperature control can be necessary as local blood flow may vary with temperature. Temperature control can be achieved by placing one or more heaters in the unit contacting the patient and a temperature feedback system in the main instrument.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A total hemoglobin measurement system for measuring total hemoglobin in human tissue comprising:
   a signal generator for generating a digital modulation signal representing a code sequence;
   an optical illumination source coupled to said signal generator for receiving said digital modulation signal and configured for transmitting a modulated optical signal along an optical transmission path to said human tissue in response to said digital modulation signal;
   a detector configured to be optically coupled to said human tissue for receiving said modulated optical signal after transmission through the optical transmission path through said human tissue;
   a processor coupled to said detector for deriving a temporal transfer characteristic for said optical signal received by said detector and for determining said total hemoglobin based on said temporal transfer characteristic;
   a second signal generator for generating a second digital modulation signal representing a second code sequence, wherein said second code sequence and said code sequence have the same ordering of code elements and begin at different code elements; and
   a second optical illumination source coupled to said second signal generator for receiving said second digital modulation signal and configured for transmitting a second modulated optical signal to said human tissue in response to said second digital modulation signal.

2. The total hemoglobin measurement system of claim 1 further comprising:
   a delay component optically coupled to said optical illumination source for increasing length of said optical transmission path.

3. The total hemoglobin measurement system of claim 2 wherein said delay component further comprises a reflective surface.

4. The total hemoglobin measurement system of claim 1 wherein said code sequence further comprises multiple identical code sequences of a single code sequence.

5. The total hemoglobin measurement system of claim 1 wherein said code sequence is circular.

6. The total hemoglobin measurement system of claim 1 wherein said code sequence is orthogonal.

7. The total hemoglobin measurement system of claim 1 wherein said code sequence is unipolar.

8. The total hemoglobin measurement system of claim 1 wherein said code sequence is a Galois code.

9. The total hemoglobin measurement system of claim 1 wherein said code sequence is a maximal-length sequence.

10. A method for measuring total hemoglobin in a human tissue comprising:
    generating a digital modulation signal associated with a code sequence;
    generating a modulated optical signal based on said digital modulation signal;
    transmitting said modulated optical signal to said human tissue;
    receiving a modified version of said modulated optical signal after transmission through said human tissue;
    deriving a temporal transfer characteristic for said modified version of said modulated optical signal;
    calculating said total hemoglobin based on said temporal transfer characteristic;
    delaying said code sequence to generate a second code sequence;
    generating a second digital modulation signal associated with said second code sequence;
    generating a second modulated optical signal based on said second digital modulation signal;
    transmitting said second modulated optical signal to said human tissue;
    receiving a second modified version of said second modulated optical signal after transmission through said human tissue; and
    deriving a second temporal transfer characteristic for said second modified version of said second modulated optical signal.

11. The method of claim 10 further comprising:
    delaying said modulated optical signal to reduce noise effects.

12. The method of claim 10 further comprising:
    determining an absorption coefficient of said human tissue from said temporal transfer characteristic.

13. The method of claim 10 wherein said code sequence is circular.

14. The method of claim 10 further comprising:
    determining a first absorption coefficient during systole based on said temporal transfer characteristic; and
    determining a second absorption coefficient during diastole based on said temporal transfer characteristic.

15. The method of claim 10 wherein said code sequence is orthogonal.

16. A total hemoglobin measurement system for measuring total hemoglobin in human tissue comprising:
    means for generating a digital modulation signal associated with a code sequence;
    means for generating a modulated optical signal based on said digital modulation signal;
    means for transmitting said modulated optical signal to said human tissue;
    means for receiving a modified version of said modulated optical signal after transmission through said human tissue;
    means for deriving a temporal transfer characteristic for said modified version of said modulated optical signal;
    means for calculating said total hemoglobin based on said temporal transfer characteristic;
    means for delaying said code sequence to generate a second code sequence;
    means for generating a second digital modulation signal associated with said second code sequence;
    means for generating a second modulated optical signal based on said second digital modulation signal;
    means for transmitting said second modulated optical signal to said human tissue;
    means for receiving a second modified version of said second modulated optical signal after transmission through said human tissue; and
    means for deriving a second temporal transfer characteristic for said second modified version of said second modulated optical signal.

* * * * *